Figure 1A:
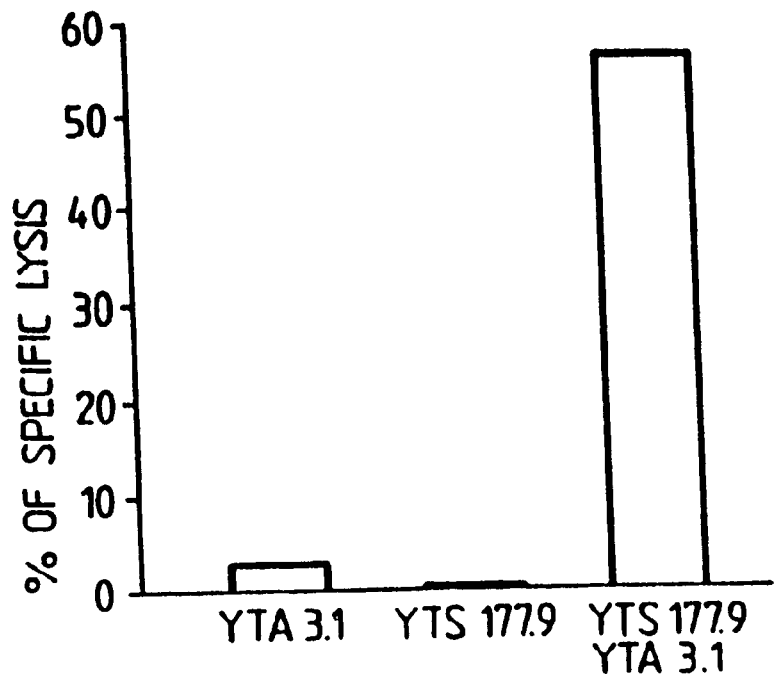

United States Patent [19]

Cobbold et al.

[11] Patent Number: 6,056,956
[45] Date of Patent: *May 2, 2000

[54] NON-DEPLETING ANTI-CD4 MONOCLONAL ANTIBODIES AND TOLERANCE INDUCTION

[75] Inventors: Stephen Paul Cobbold; Herman Waldmann, both of Cambridge, United Kingdom

[73] Assignee: Glaxo Wellcome Inc., Research Triangle Park, N.C.

[ * ] Notice: This patent is subject to a terminal disclaimer.

[21] Appl. No.: 08/470,421

[22] Filed: Jun. 6, 1995

Related U.S. Application Data

[63] Continuation of application No. 08/289,532, Aug. 12, 1994, Pat. No. 5,690,933, which is a continuation of application No. 08/181,170, Jan. 13, 1994, abandoned, which is a continuation of application No. 08/047,344, Mar. 29, 1993, abandoned, which is a continuation of application No. 07/768,868, Jul. 27, 1991, abandoned.

[30] Foreign Application Priority Data

May 31, 1989 [GB] United Kingdom .................... 8912497

[51] Int. Cl.$^7$ .......................... A61K 39/395; A61K 37/02
[52] U.S. Cl. .................................... 424/144.1; 424/143.1; 424/153.1; 424/154.1; 424/173.1; 514/11
[58] Field of Search .............................. 424/130.1, 134.1, 424/141.1, 143.1, 144.1, 153.1, 154.1, 173.1; 530/387.1, 388.1, 388.22, 388.7, 388.73, 388.78

[56] References Cited

U.S. PATENT DOCUMENTS 4,681,760  7/1987  Fathman .
4,695,459  9/1987  Steinman et al. .
5,690,933  11/1997  Cobbold et al. .

OTHER PUBLICATIONS

M. Bartholomew, et al, "Functional Analysis of the Effects of a Fully Humanized anti–CDR Antibody on Resting and activated Human T Cells", *Immunology* 85:41 (1995), pp. 41–48.
Yedida Sharabi, et al, "Mixed Chimerism and Permanent Specific Transplantation Tolerance Induced by a Nonlethal Preparative Regimen", *The Journal of Experimental Medicine*, vol. 169, Feb. 1989, pp. 493–502.
Schmidt et al. Nervenarzt 67: 170–176 (1996).
Schmidt et al. Nervenarzt 67: 170–176 (1996) English translation.
Levy et al. Arthritis Rheumatsm 39(9 suppl) S122, 1996 #574.
Choy et al. Arthritis Rheumatym 39(9 suppl) S244, 1996 #1301.
Panayi et al. Arthritis Rheumatsm 39(9 suppl) S244, 1996 #1300.
Connolly et al. Arthritis Rheumatism 39 (9 suppl) S245, 1996 #1302.
Watson et al. Tissue Antigens 43: 155–162 (1994).
Watson et al. Transplant. Proc. 27(1): 123–124 (1995).
Bach et al. Immunol. Today 14: 421–425 (1993).
Russell et al BMJ 305: 1424–1429 (1997).
Nossol n Paul (ed) Fundamental Immunology 2$^{nd}$ Ed. Raven Press, NY 1989 pp 571–586.
Watson et al. J Surg. 80: 1389–1392 (1993).
Chen et al. Transplant Proc. 26: 2433–2434 (1994).
Jolliffe Intern Riv Immunol. 10:241–250 (1993).
Waldmann Am I Kid Dis XI(2) 154–158 (1988).
I. Harris et al. TIBTECH 11: 42–44 (1993).
Waldmann Science 252: 1657–1662 (1989).
Riethmuller et al., *Immunological Series*, 59, Ed. Bach, pp. 261–269 (1993).
Morel et al., *Immunological Series*, 59, pp. 271–276 (1993).
Riethmuller et al., *Immunological Reviews 1992*, No. 129, pp. 81–104.
Benjamin et al., J. Exp. Med., 163 (1986), pp. 1539–1552.
Benjamin and Waldmann, Nature 320 (1986), pp. 449–451.
Benjamin et al., Eur. J. Immunol. 18 (1988), pp. 1079–1088.
Carteron et al., *J. Immunol. 140* (1988) pp. 713–716.
Cobbold et al., Nature 312 (1984) pp. 548–551.
Cobbold et al., Eur. J. Immunol. 20 (1990) pp. 2747–2755.
Goronzy et al., J. Exp. Med. 164 (1986) pp. 911–925.
Gutstein et al., *J. Immunol.* 137 (1986) pp. 1127–1132.
Gutstein and Wofsey, J. Immunol. 137 (1986) pp. pp. 3414–3419.
Kirkman et al., J. Exp. Med., 162 (1985), pp. 358–362.
Qin et al., J. Exp. Med. 169 (1989), pp. 779–794.
Qin et al., Eur. J. Immunol. 20 (1990), pp. 2737–2745.
Ranges et al., J. Exp. Med. 162 (1985), pp. 1105–1110.
Sedgwick et al., J. Neuroimmunol., 13 (1986), pp. 217–222.
Waldmann, Annual Reviews Immunology 7 (1989), pp. 407–444.
Waldor et al., Science 227 (1985), pp. 415–417.
Wofsey et al., J. Immunol. 134 (1985), pp. 852–856.
Wofsey et al., J. Immunol. 135 (1985), pp. 1698–1701.
Wofsey and Seaman, J. Exp. Med. 161 (1985), pp. 378–391.
Waldmann et al in Progress in Immunology vol. VII, Proceedings of the 7th International Congress of Immunology Berlin 1989, F. Melchers et al., eds, Springer–Verlag (1989), pp. 147–155.
Waldmann et al., in Cold Spring Harbor Symposium on Quantitative Biology:Immunological Recognition LIV, Cold Spring Harbor Laboratory Press (1989), pp. 885–892.
Jonker et al., Transplant Proc. XIX (1987), pp. 4308–4314.
Charlton et al., Immunol. Cell Biol. 67(1) (1989), pp. 1–7.
Carteron et al.,, J. Immunol., 142,(1989), pp. 1470–1475.
Qin et al., Eur. J. Immunol., 17 (1987), pp. 1159–1165.

*Primary Examiner*—Christina Y. Chan
*Assistant Examiner*—Phillip Gambel
*Attorney, Agent, or Firm*—Nixon & Vanderhye P.C.

[57] ABSTRACT

Tolerance to an antigen is induced in a subject by administering a non-depleting CD4 monoclonal antibody and a non-depleting CD8 monoclonal antibody. Tolerance to the antigen can be induced under cover of these antibodies. A depleting CD4 monoclonal antibody and/or a depleting CD8 monoclonal antibody may be administered prior to the non-depleting antibodies.

9 Claims, 11 Drawing Sheets

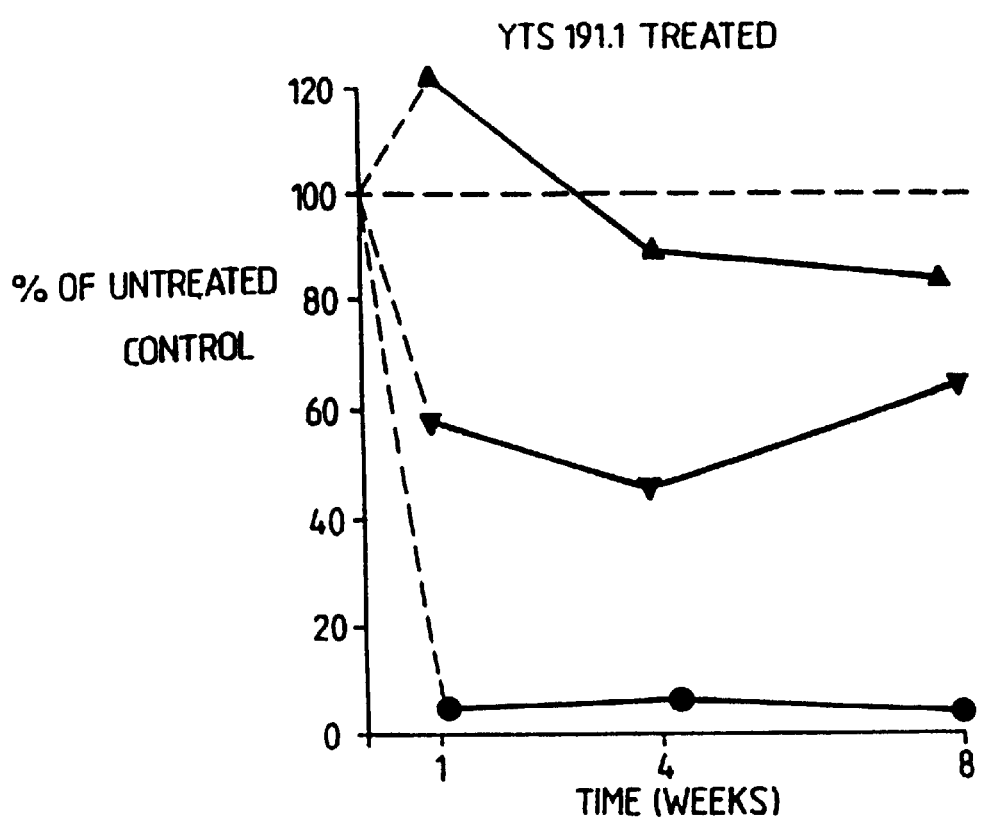
*Fig.2a.*
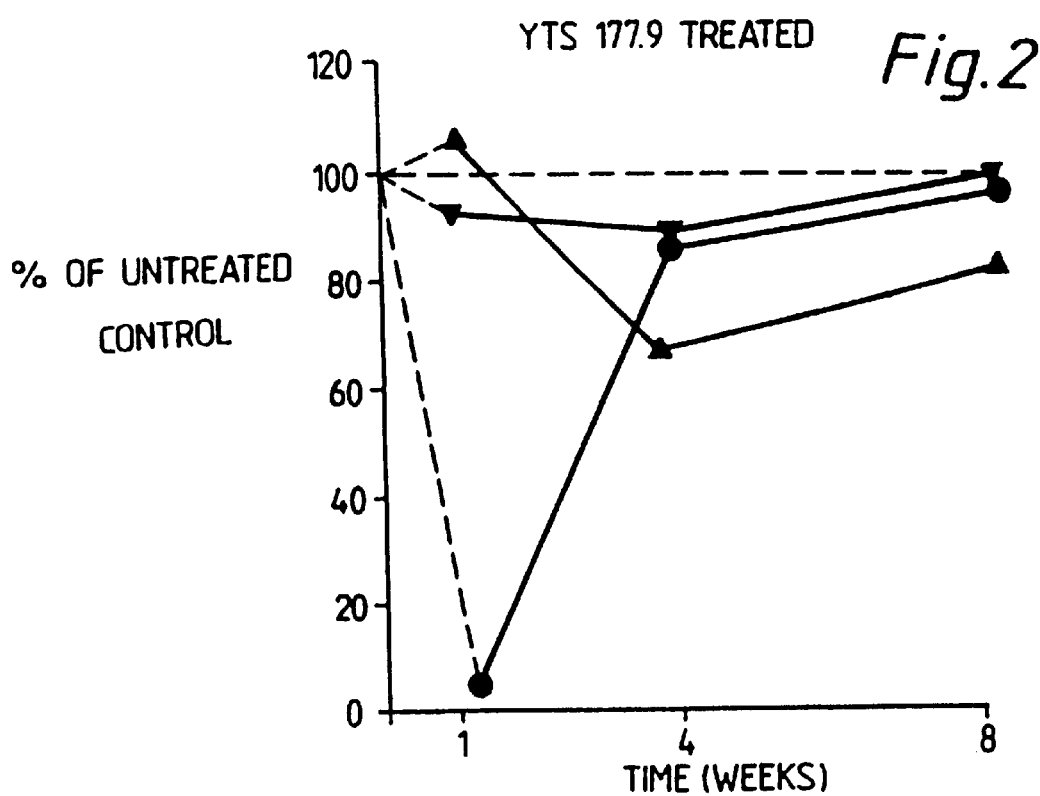
*Fig.2.b.*

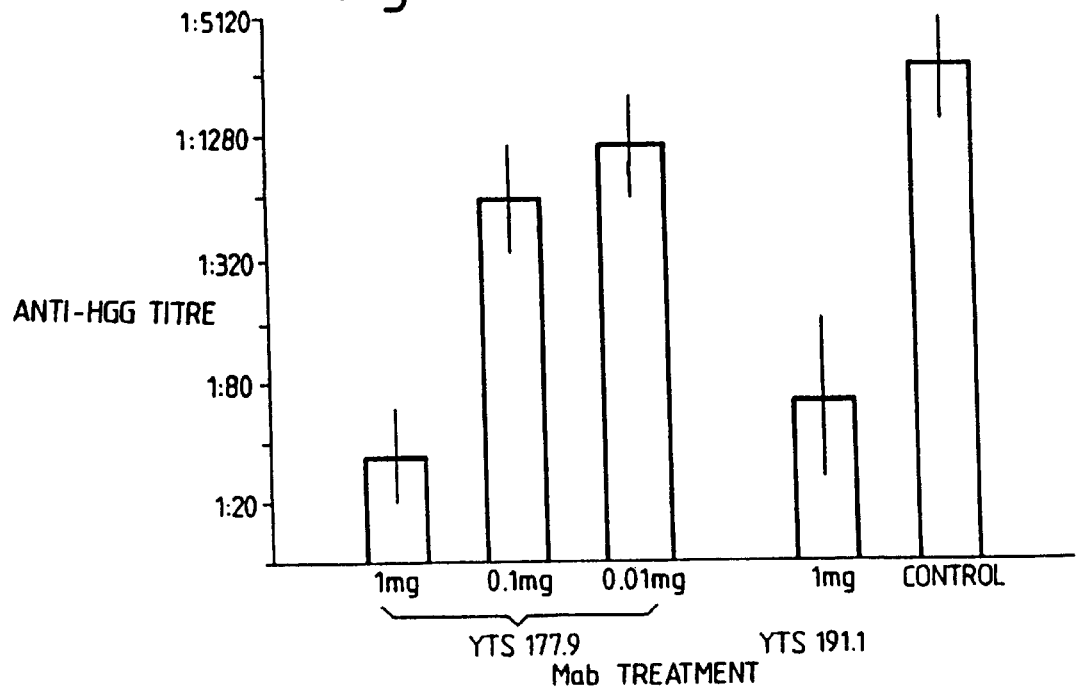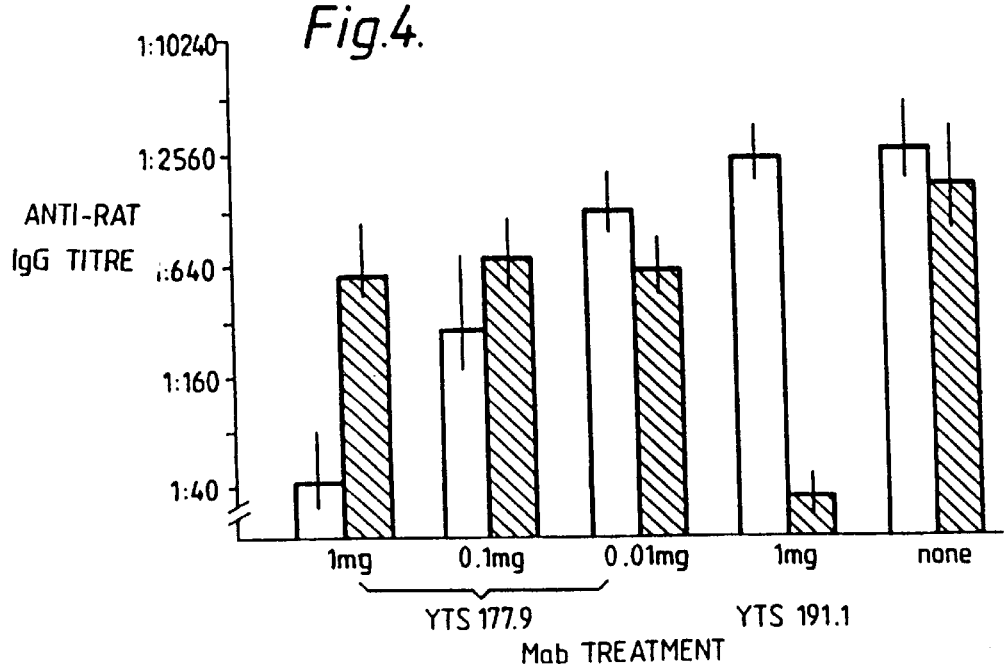

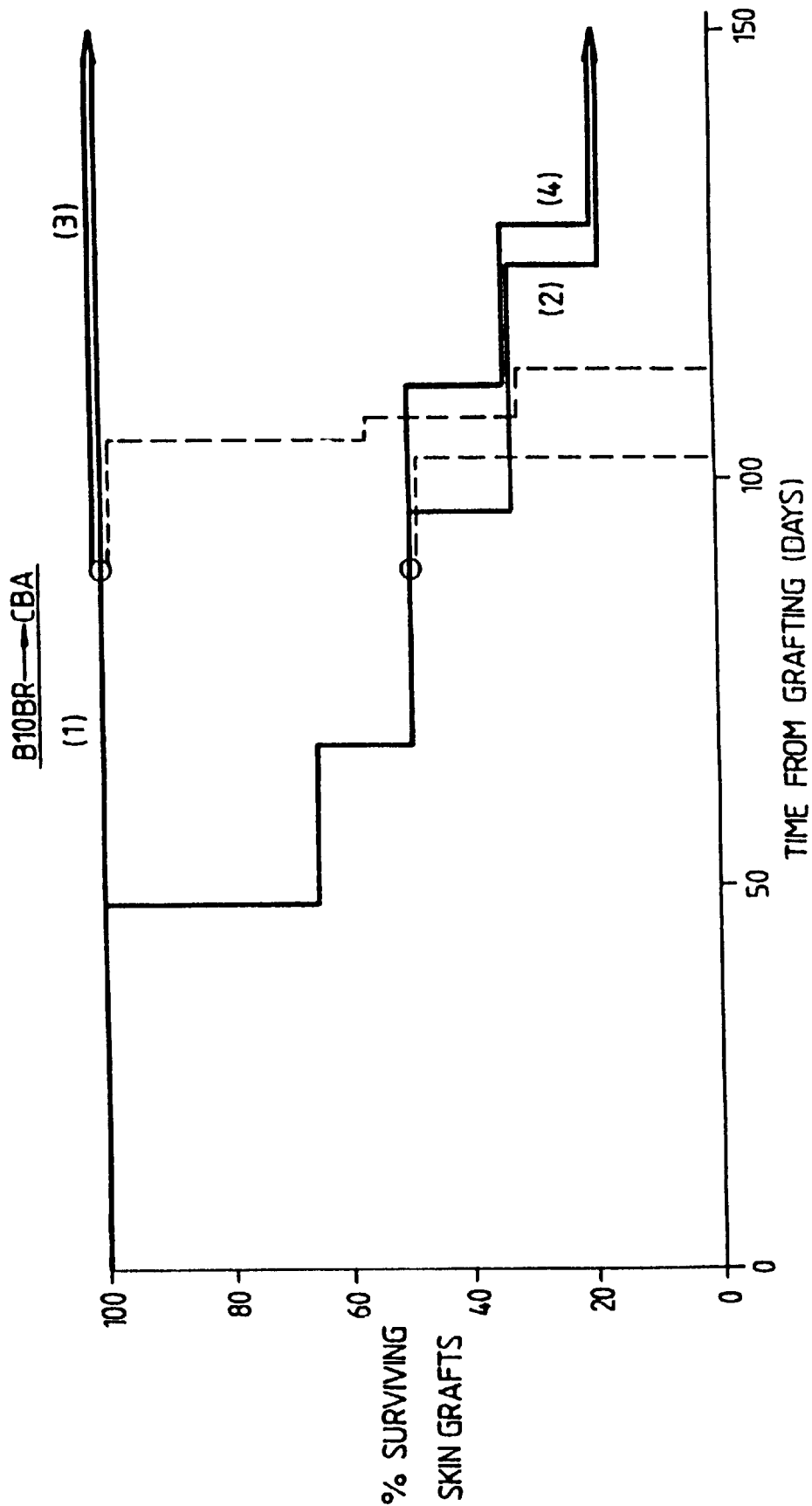

NON-DEPLETING ANTI-CD4 MONOCLONAL ANTIBODIES AND TOLERANCE INDUCTION

This is a continuation of application Ser. No. 08/289,532, filed Aug. 12, 1994, now U.S. Pat. No. 5,910,933 which is a continuation of Ser. No. 08/181,170, filed Jan. 13, 1994, now abandoned, which is a continuation of Ser. No. 08/047,344, filed Mar. 29, 1993, now abandoned, which is a continuation of Ser. No. 07/768,868, filed Jul. 27, 1991, now abandoned.

This invention relates to tolerance induction using monoclonal antibodies.

Tolerance to foreign antigen or tissue, or self antigen or tissue is a state whereby an otherwise normal, mature immune system is specifically unable to respond aggressively to that antigen/tissue which it therefore treats like a normal (non-diseased) body tissue/component, yet at the same time it can respond aggressively to foreign or diseased antigens/tissues to which it has not been specifically made tolerant by the natural process of self tolerance or by therapeutic tolerance induction procedures. A test for tolerance usually requires a demonstration that the tolerant individual fails to become immune to the specific antigen/tissue when one or preferably more attempts to immunize are made at a later time when the same individual can be shown to respond to an irrelevant antigen/tissue.

Monoclonal antibodies (mAb) against the murine CD4 (L3T4) antigen have proven to be potent immunosuppressive agents for the control of humoral immunity, transplant rejection and autoimmunity. In addition, CD4 mAbs have been shown to create a tolerance-permissive environment in vivo with which can be achieved tolerance to certain soluble protein antigens as well as transplantation antigens. However, the mechanism(s) by which CD4 mAbs produce these effects are still not clear. In most previous reports, immunosuppression was obtained under conditions that depleted target cells in vivo. A simple interpretation was that the immune suppression so achieved was due to the absence of CD4 T cells.

On the other hand, in vitro work has demonstrated that CD4 (and CD8) mAbs could affect lymphocyte functions simply through binding to the antigen on the cell surface without cell lysis. In addition, immunosuppression and tolerance induction has been obtained in with the use of sublytic concentrations of CD4 mAbs and by F(ab')$_2$ CD4 mAb fragments which suggest that for mAb-mediated immune regulation, depletion of target cells may not be essential.

Previous studies have used antibodies that deplete CD4 cells. We have now found that non-depleting CD4 and CD8 antibodies can also produce tolerance to foreign immunoglobulins, bone marrow and skin grafts. Indeed, this observation has general applicability to all antigens. Further, we have found that administration of a depleting CD4 mAb and/or a depleting CD8 mAb prior to administration of the non-depleting mAbs can be beneficial in creating a tolerance-permissive environment.

The present invention therefore provides products containing a non-depleting CD4 mAb and a non-depleting CD8 mAb as a combined preparation for simultaneous, separate or sequential use in inducing tolerance to an antigen. A non-depleting CD4 mAb for use in a method of treatment of the human or animal body by surgery or therapy and a non-depleting CD8 mAb for use in a method of treatment of the human or animal body by surgery or therapy also form part of the invention. The invention further provides:

non-depleting CD4 and CD8 mAbs for use together in a method of treatment of the human or animal body by surgery or therapy, especially for use in inducing tolerance to an antigen; and a pack comprising as separate components a non-depleting CD4 mAb and a non-depleting CD8 mAb, typically in separate compartments.

By administering non-depleting CD4 and CD8 mAbs together, tolerance can be conferred to a primary antigen in a patient. The CD4 and CD8 mAbs can be used to treat autoimmune diseases and to prevent graft rejection without the need for long term immunosuppressive chemotherapy. Tolerance to a graft such as an organ graft or bone marrow transplantation can be achieved.

There are advantages of using non-depleting mAbs in vivo. For example, injection of a short course of non-depleting mAbs allows quicker recovery of competent cells from blockade and therefore may lessen the risk of opportunistic infection and other complications due to immune deficiency (e.g. leukemia relapse after T-depleted bone-marrow transplantation) following m treatment. In addition, it is now known that CD4 cells can be further divided into different functional subsets, some of which may be involved in immune regulation. Bulk elimination of T cells may of course result in immune suppression, but it may also destroy an possible influence of CD4+ regulatory cells. Therefore, a more subtle manipulation may be more beneficial for guiding the immune system to a desired state.

Tolerance may preferably be attained by administering first to a patient depleting CD4 and/or CD8 mAbs. The invention therefore further provides:

non-depleting CD4 and CD8 mAbs and depleting CD4 and/or CD8 mAbs for use together in a method of treatment of the human or animal body by surgery or therapy, more specifically in inducing tolerance to an antigen;

products containing a non-depleting CD4 mAb, a non-depleting CD8 mAb and either or both of a depleting CD4 mAb and a depleting CD8 mAb as a combined preparation for simultaneous, separate or sequential use in inducing tolerance to an antigen; and a pack comprising a non-depleting CD4 mAb, a non-depleting CD8 mAb and either or both of a depleting CD4 mAb and a depleting CD8 mAb, typically each in a separate compartment.

A combination of non-depleting CD4 and CD8 mAbs can be used to induce tolerance to any antigen without the need for other immunosuppressive agents. A non-depleting mAb is a mAb which depletes fewer than 50%, for example from 10 to 25% and preferably less than 10% of target cells in vivo. They may be used to induce tolerance to a Class I antigen or to a Class II antigen or to an antigen presented by a Class I or Class II antigen. They may be used to induce tolerance to both antigens. In the case of a transplant, for example, Class I and Class II major histocompatibility (MHC) antigens and non-MHC or minor histocompatibility (minors) antigens may be presented. Apart from transplantation antigens, the present invention can be used to induce tolerance to globular proteins, glycoproteins such as immunoglobulins, materials carried on particles such as pollen proteins, polypeptides intended for therapeutic use such as interferon, interleukin-2 or tumour necrosis factor, or hormone replacements such as leutinizing hormone, its analogues and antagonists. Further specific antigens to which tolerance can be conferred include synthetic peptide analogues of protein therapeutic agents which are used for receptor block aid and alloantigens.

It is alloantigens which are considered to be responsible for rejection of foreign tissue in tissue transplants or skin grafts.

The mAbs which may be used are mAbs which are specific for the CD4 cell surface antigen (CD4 mAb) or for the CD8 cell surface antigen (CD8 mAb). By CD4 and CD8 ms we mean not only mAbs specific for the human CD4 and CD8 surface antigens but also mAbs specific for the corresponding surface antigens in other species such as the L3T4 antigen in mice which is the murine equivalent of the human CD4 antigen. The mAbs are typically of the $IgG_2$ Class such as rat $IgG_{2a}$, mouse $IgG_{2b}$ or human $IgG_2$, but may be human $IgG_4$. mAb fragments comprising the antibody binding site may be used, such as Fab and $F(ab)_2$ fragments.

The CD4 and CD8 mAbs are administered together to a host. They may be administered as part of the same formulation or as separate formulations. Typically both mAbs are administered from 1 to 7 times a week, preferably from 1 to 4 times a week, for example three times a week, for from 2 to 4 weeks, preferably for 3 weeks. An effective amount of the non-depleting mAbs is given. Testing for saturating amounts of antibody in serum should indicate that sufficient antibody is present. Enough of each non-depleting mAb is consequently administered to induce a tolerance-permissive environment in a subject under treatment. The CD4 and CD8 cells can thus be blocked.

The amount of non-depleting CD4 mAb and of non-depleting CD8 mAb administered to a patient depends upon a variety of factors including the age and weight of a patient, the condition which is being treated and the antigen(s) to which it is desired to induce tolerance. In a model mouse system from 1 µg to 2 mg, preferably from 400 µg to 1 mg, of a mAb is administered at any one time. In humans from 1 to 400 mg, such as from 3 to 30 mg, for example from 5 to 20 mg, of antibody may be given. A CD11a m, a non-depleting mAb, may be used in addition to CD4 and CD8 mAbs or in place of either or both of the CD4 or CD8 mAbs.

A foreign antigen(s) to which it is desired to induce tolerance can be administered to a host from up to 5 days before a course of non-depleting CD4 and CD8 mAbs is commenced to up to 5 days or even 2 to 3 weeks after the course has been completed. Generally, however, an antigen is administered within the first 14 days of the course commencing, typically within 7 days of the course commencing. The antigen can be given at the time the course of CD4 and CD8 mAb treatment is commenced.

Tolerance can therefore be induced to an antigen in a host by administering non-depleting CD4 and CD8 mAbs and, under cover of the mAbs, the antigen. A patient may be operated on surgically under cover of the non-depleting CD4 and CD8 mAbs to be given a tissue transplant such as an organ graft or a bone marrow transplant. Also, tolerance may be induced to an antigen already possessed by a subject. Long term specific tolerance can be induced to a self antigen or antigens in order to treat autoimmune disease such as multiple sclerosis or rheumatoid arthritis. The condition of a patient suffering from autoimmune disease can therefore be alleviated.

Persistant antigen is required to maintain tolerance. A tissue graft, for example, supplies the antigen to maintain tolerance to itself. The same applies to self (auto) antigens in the treatment of autoimmune diseases. In the case of extraneous foreign antigen such as allergens, antigen reminders can be given at regular intervals.

It may be preferable to treat a host with a depleting CD4 mAb and/or a depleting CD8 m before commencing treatment with non-depleting mAbs. A depleting mAb is a mAb which depletes more than 50%, for example from 90 to 99%, of target cells in vivo. Depleting antibodies include rat $IgG_{2b}$, or $IgG_1$, mouse $IgG_{2a}$ and human $IgG_1$ and $IgG_3$. A depleting CD4 mAb and/or a depleting CD8 mAb may therefore be used to reduce the relevant population of T cells. The non-depleting mAbs therefore have fewer T cells to work on. Depletion may alternatively be achieved by conventional immunosuppressive therapy such as administration of another mAb such as CAMPATH (Trade Mark) 1, steroids, cyclosporin, ALG (anti-lymphocyte globulin) or irradiation.

The level to which a population of T cells is reduced by a depleting mAb may depend upon the antigen(s) to which it is wished to achieve tolerance. It may be preferable to reduce the T cell population further for difficult antigens, for poorly matched tissue grafts, where recipients have been previously exposed to donor antigens and are primed (for example multiply transfused patients) or in autoimmune diseases where the patients are both primed and undergoing continuous activation of their autoimmune state. A poor tissue match, for example, is where one or more Class I major histocompatibility antigens do not match.

It may therefore be necessary to reduce a population of CD4-positive helper T cells to less than about 70%, for example less than about 50%, 20% or even 10%, of their normal level. The more difficult it is likely to be to achieve tolerance, the greater the amount of depletion it is desirable to achieve. CD8-positive T cells may be depleted in the same way.

The depleting CD4 mAb and/or depleting CD8 mAb is typically administered from 1 to 7 times a week, preferably from 2 to 4 times a week, for example three times a week or once or twice, preferably once, from 1 to 7 days, for example from 1 to 5 days, before commencement of the treatment with non-depleting CD4 and CD8 mAbs. An antigen to which it is desired to induce tolerance may be administered at the same time as, or within 5 days of, administration of the depleting mAb. The amount of depleting mAb which is given depends upon a variety of factors including the level to which it is desired to reduce the relevant population of T cells, the age and weight of a patient, the condition which is being treated and the antigen(s) to which it is desired to induce tolerance. In a mouse model system, dose of from 1 µg to 2 mg, preferably from 400 µg to 1 mg, of a depleting mAb may be given. In humans, from 1 to 400 mg, such as from 3 to 30 mg, for example from 5 to 20 mg, of antibody may be given.

The depleting and non-depleting CD4 and CD8 mAbs can be raised in any convenient manner. They may be made by conventional methods of fusing immune rat spleen cells to a rat myeloma cell line such as Y3/Ag 1.2.3. (Clark and Waldmann, chapter 1 of "Monoclonal Antibodies", which is a book edited by P. C. L. Beverley in a series "Methods in Hematology", Longman (Churchill Livingstone), 1986). Any other method may be employed such as by fusing immunised mouse spleen cells with a mouse myeloma, a rat myeloma or human myeloma or by recombinant DNA methodologies.

All mAb administrations are given parenterally, for example intravenously. The mAbs are generally being given by injection or by infusion. For this purpose a mAb is formulated in a pharmaceutical composition containing a pharmaceutically acceptable carrier or diluent. Any appropriate carrier or diluent may be used, for example isotonic saline solution. When specific antigens to which it is wished to confer tolerance are given, these may be administered parenterally, for example intravenously, intramuscularly or subcutaneously. The antigen is typically formulated with a pharmaceutically acceptable carrier or diluent as above.

The respective hybridomas producing mAbs YTS 177.9, YTS 191.1, YTS 105.18 and YTS 169.4 were deposited at the European Collection of Animal Cell Cultures, Porton Down, G. B. on May 30, 1990 under accession numbers ECACC 90053005, ECACC 87072282, ECACC 90053004 and ECACC 87072284.

The following Examples illustrate the invention. In the accompanying drawings:

FIG. 1 shows synergy and interference of complement lysis by combinations of rIgG2a and rIgG2b Mabs. CBA/Ca thymocytes labelled with $^{51-}$Cr (30 μCi/ml) were incubated with Mabs as indicated under each bar and 2% guinea pig serum as the complement source. Mab concentration: (A) 5 μg/ml; (B) 25 μg/ml of the Mabs used.

FIG. 2 shows the results of injection of rIgG2a CD4 in vivo without T cell depletion. ATX CBA/Ca mice (n=3) were given a single injection of the indicated Mabs (2 mg/mouse) and bled at 1, 4 and 8 weeks later. BPL were stained with biotinylated Mabs against CD4 (YTA 3.1 ●), CD8 (YTS 156.7 ▲) and Thy-1 (YBM 29.2 ▼), followed by streptavidin-FITC. The results were analysed by flow cytometry and the percentage of each population was calculated using that of the untreated control on the test day as 100%.

FIG. 3 shows how tolerance to HGG was induced by IgG2a CD4 Mab YTS 177.9. Normal CBA/Ca mice were given YTS 177.9 or YTS 191.1, at doses indicated on days −1, 0 and 1. 1 mg heat-aggregated HGG was injected on day 0. The mice were rechallenged with 0.5 mg HGG on days 28 and 35. Control mice received 1 mg of YTS 177.9 as others, but immunized with HGG only on days 28 and 35. Serum anti-HGG titres were measured on day 45 by an ELISA assay.

FIG. 4 shows the results of injection of YTS 177.9 to induce specific tolerance to rat IgG2a. Normal CBA/Ca mice were given 3 injections of YTS 177.9 or YTS 191.1 at the indicated doses on 3 consecutive days. 6 weeks later, they were rechallenged with weekly injection of YTH 35.4 (IgG2a rat anti-human) and Campath (Registered Trade Mark) 2 (IgG2b rat anti-human), first in complete, then in incomplete Freunds adjuvant. On the tenth week, they were bled and anti-IgG2a (open-bar) and anti-IgG2b (cross-hatched bar) titres were measured with an ELISA assay using plates coated with HPLC-purified rat IgG2a and IgG2b mAbs respectively.

Figure 5:
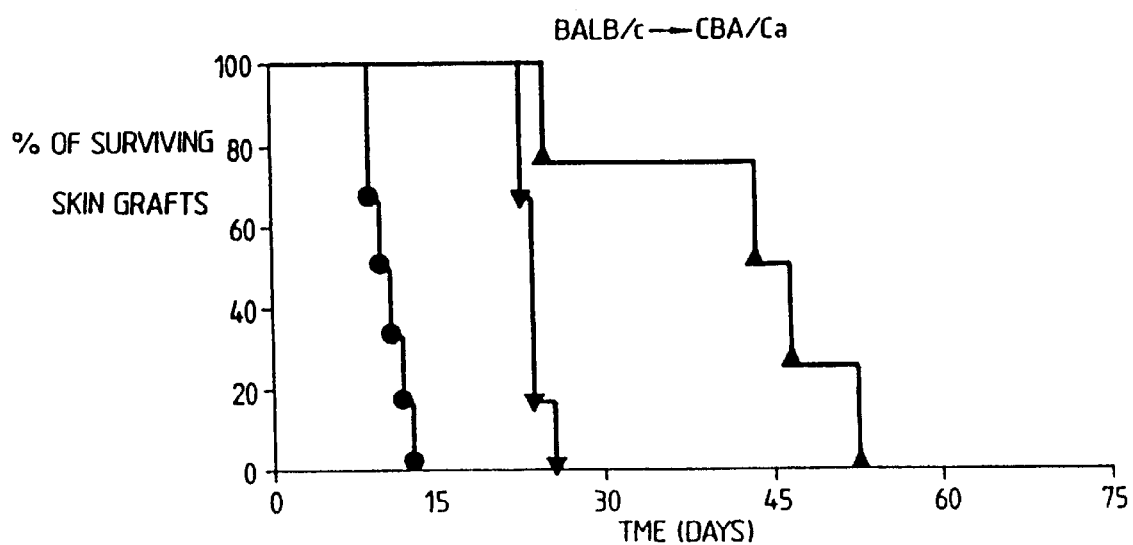

FIG. 5 shows prolonged allogeneic skin graft survival after IgG2a CD4 and CD8 Mab treatment. Normal CBA/Ca mice (n=6) were given 3 injections of YTS 177.9 and YTS 105.18 or YTS 191.1 and YTS 169.4 (total antibody, 3 mg/mouse) on days 0, 2 and 4. Full thickness BALB/c tail skin was grafted on day 0. Statistic value by Logrank method: IgG2b Mab treated (▲) v.s. non-treated control (●) p<0.005; IgG2a treated (▼) v.s. control p<0.001; v.s. IgG2b treated p<0.03.

FIG. 6 shows tolerance to allogeneic skin grafts by rIgG2a mAbs. Normal CBA/Ca mice were grafted with BLO.BR skin and received (1) a mixture of YTS 177.9 and YTS 105.18 on days 0 and 2 (2 mg/mouse total); (2) the same mAbs over 3 weeks (9 mg/mouse total). On day 89, they were regrafted with skin from B10.BR (3 and 4) and B10.D2 (dotted lines).

Figure 7A:
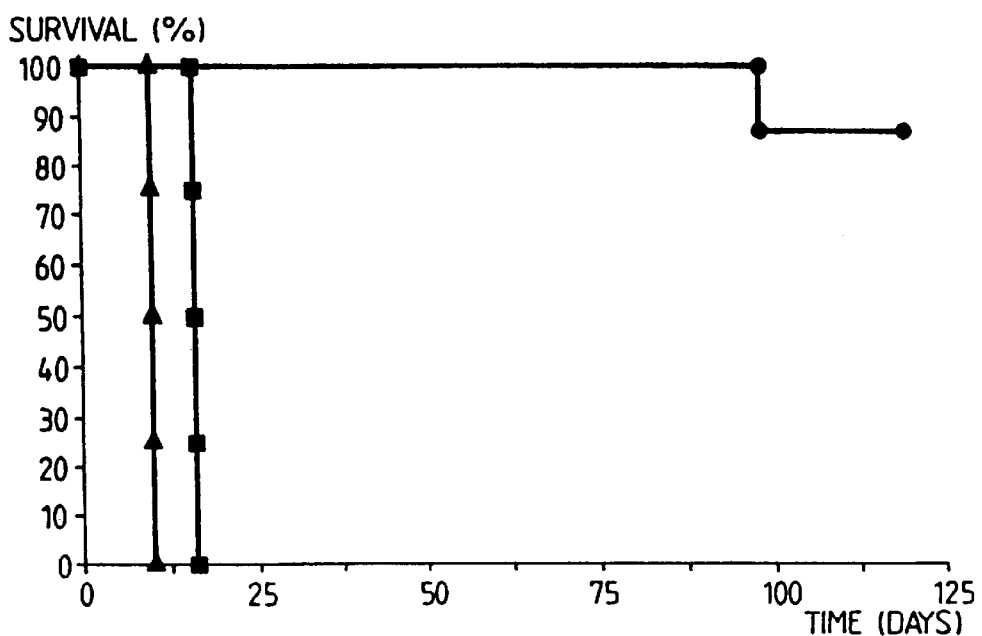
Figure 7B:
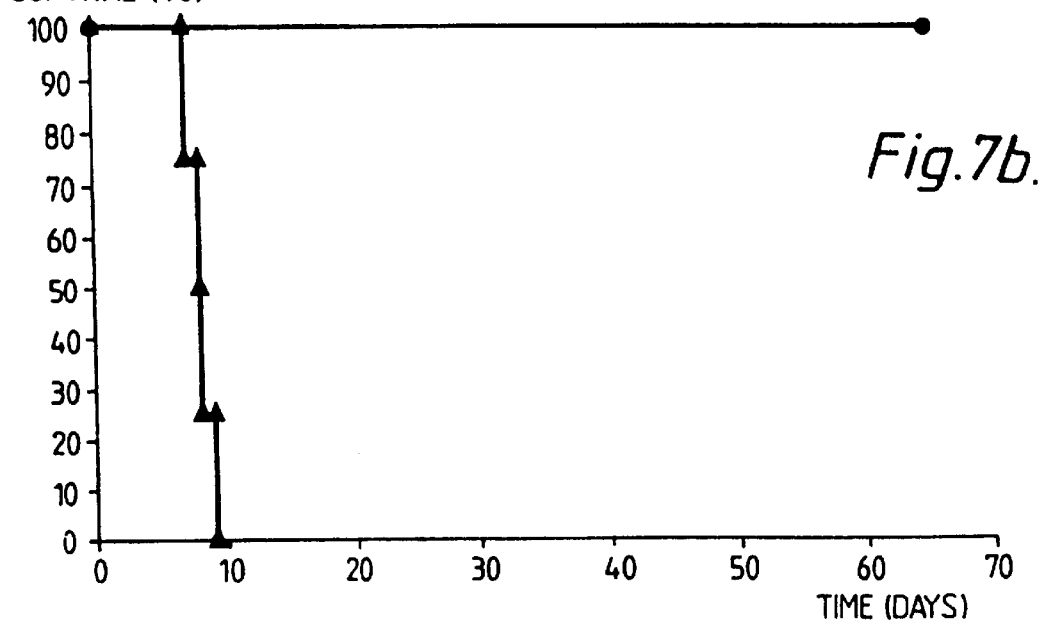

FIGS. 7A and 7B show the results of experiments investigating tolerance to bone marrow and skin grafts. FIG. 7A shows: Tolerance to B10.BR. Recipient CBA/Ca mice (n=8) were given 1–3 weeks injections of a combination of rigG$_{2a}$ CD4 and CD8 mAbs, following an infusion of $10^7$ T-depleted spleen cells and $10^7$ bone marrow cells. Control mice (n-4) were either bone marrow and saline injected or bone marrow treated only. All groups were grafted with B10.BR skin thirty days later. Chimerism of donor-allotype Ig was measured at 24 and 60 days post bone marrow transplant as 2.6±1.6 and 1.3±0.7 per cent respectively for marrow and antibody treated mice (●). Neither saline (▲) nor BM only (▼) groups showed any detectable chimerism.

FIG. 7B shows: Tolerance to AKR/J. Normal CBA/Ca recipient mice were injected for 3 weeks with a combination of rigG$_{2a}$ CD4 and rigG$_{2b}$ CD8 mAbs. $2 \times 10^7$ AKR/J bone marrow cells were infused intravenously 2 days after the beginning of mAb treatment. 4 weeks later, they were grated with AKR/J skin (●). Control mice were antibody-treated only (▲).

Figure 8:
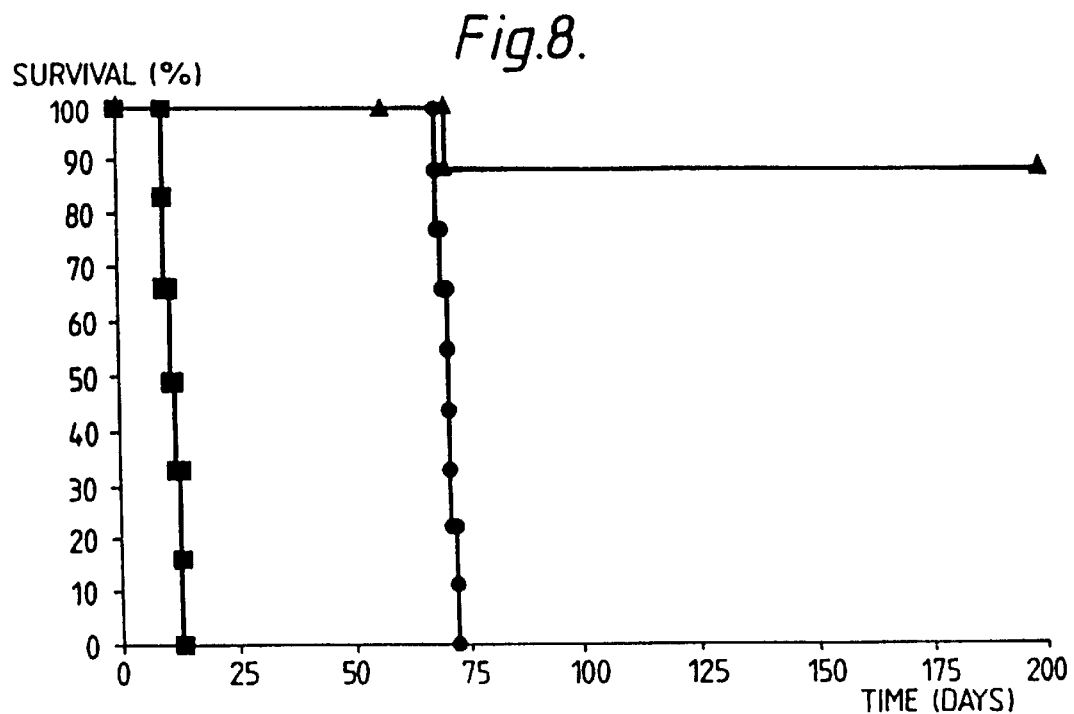

FIG. 8 Tolerance to skin grafts can be established in ATx mice. ATx mice (n=9) were injected with rigG$_{2a}$ CD4 and CD8 mAbs every other day for 2 weeks. B10.BR skin was grafted 3 days after the beginning of mAb treatment. On day 60, they were regrafted with B10.BR and BALB/c grafts (●) were rejected by ATX mice carrying B10.BR skin grafts (▲). Control ATx mice were grafted with B10.BR skin (■).

Figure 9:
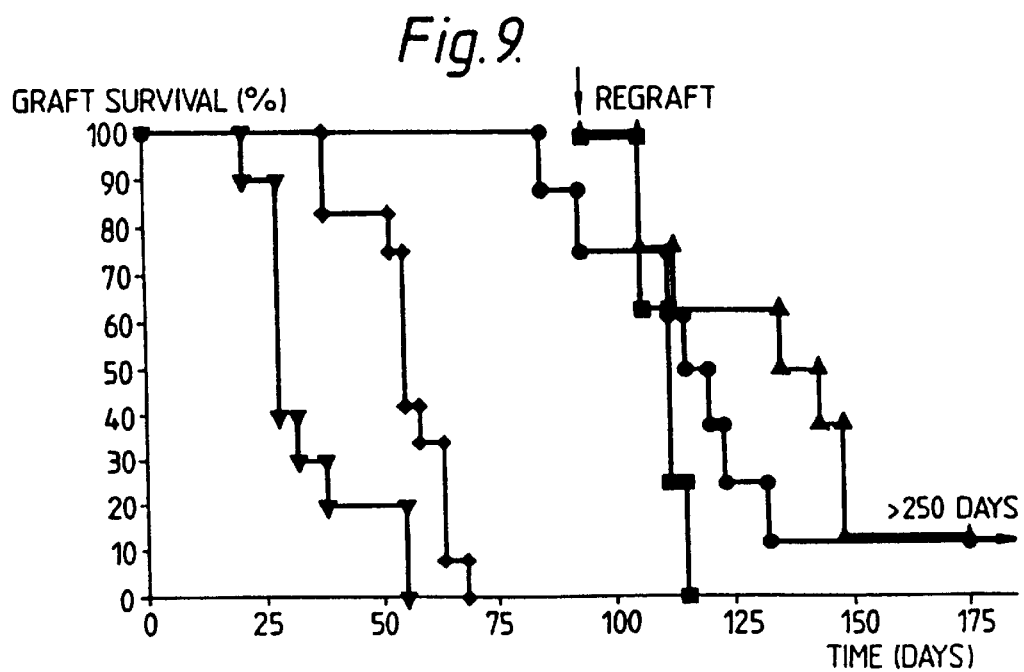

FIG. 9 shows allogeneic skin graft survival in mice treated with difference combinations of CD4 and CD8 antibodies. Recipient CBA/Ca mice, in three groups of 8–14, were grafted with BALB/c skin on day 0, and treated with monoclonal antibodies from day 0 to day 2, as described in Example 2. The first group (▼) received only rat IgG$_{2a}$ antibodies, the second (♦) received a cocktail of rat IgG$_{2b}$ antibodies, while the third group (●) was given the combination protocol of rat IgG$_{2b}$ followed by rat IgG$_{2a}$ antibodies. All mice in this third group were given new BALB/c (▲) and B10 (■) skin grafts at day 94 without further antibody.

Analysis of graft survival: IgG$_{2a}$ group MST-28 days versus IgG$_{2b}$ group MST=55 days; P<0.006: Combined protocol group original BALB/c graft MST=121 days compared to IgG$_{2a}$ or IgG$_{2b}$ groups P<0.001: Combined protocol group second BALB/c graft MST=43 days compared to third party B10 graft MST=16 days P<0.04.

Figure 10A:
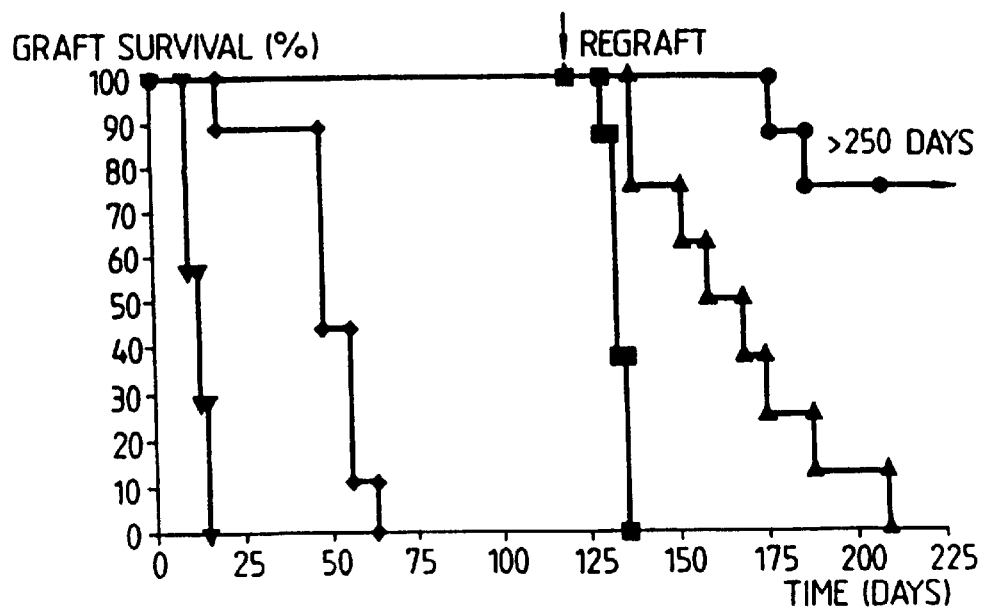
Figure 10B:
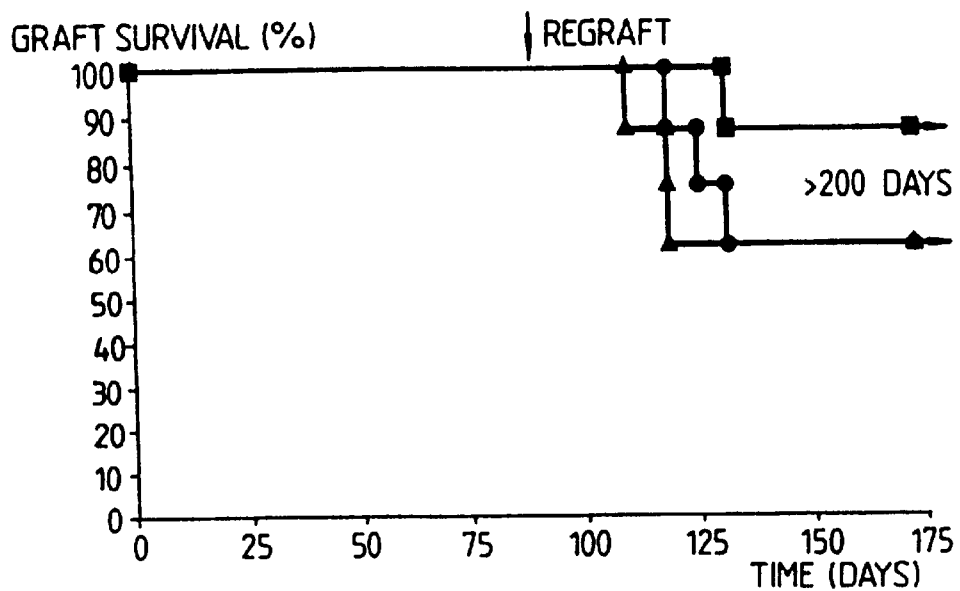
Figure 12A:
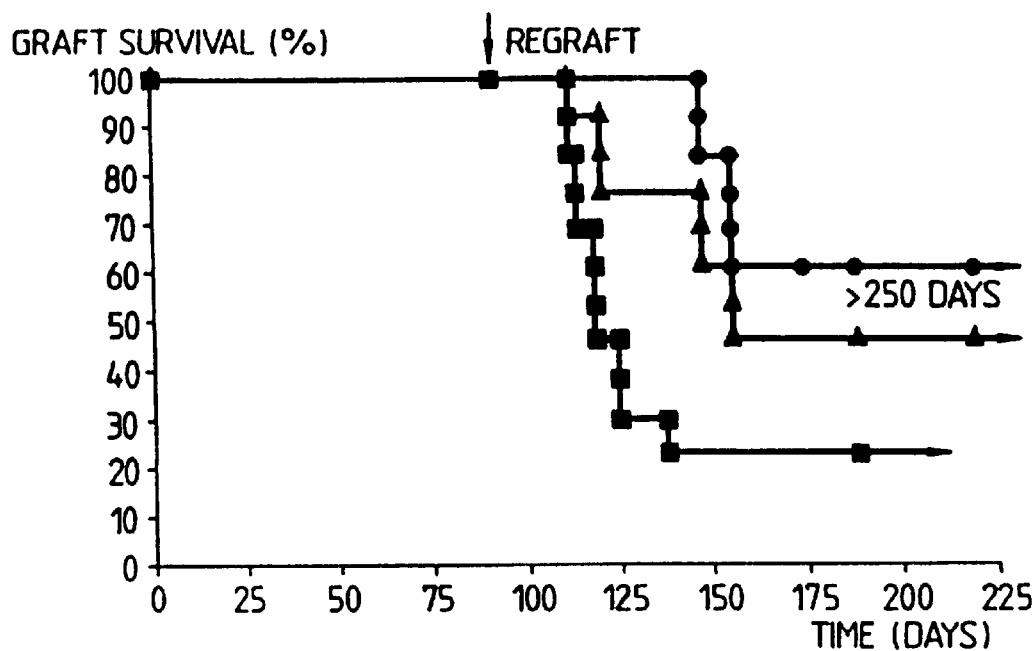
Figure 12B:
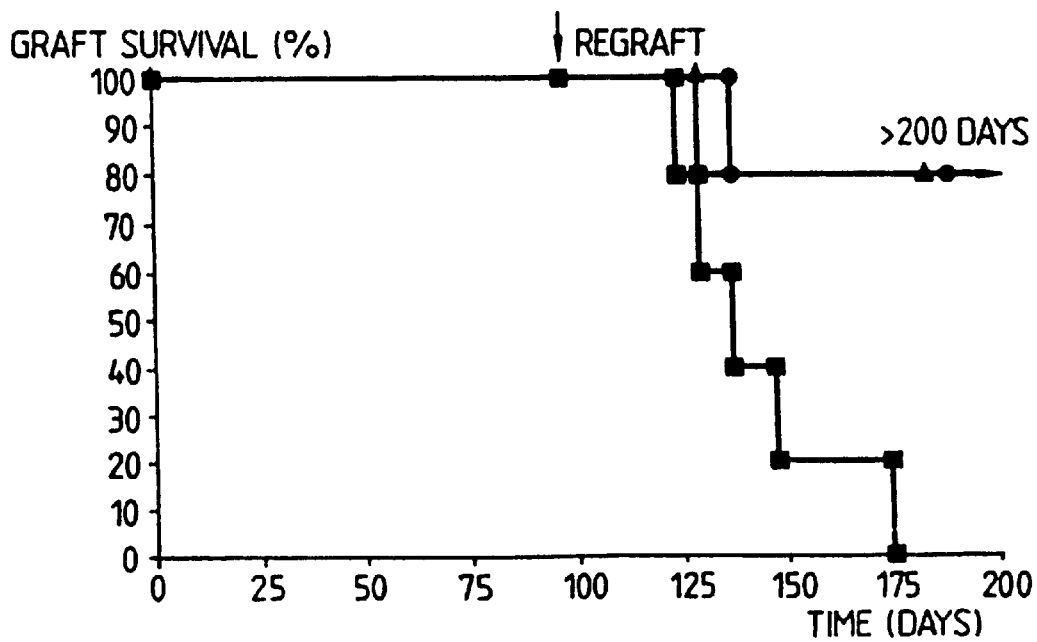
Figure 12C:
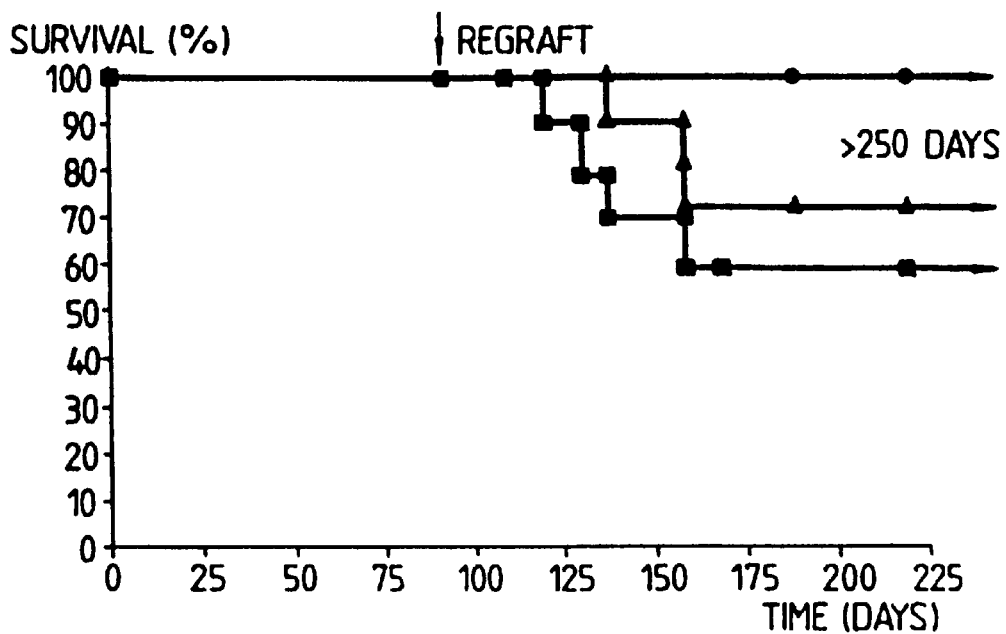
Figure 12D:
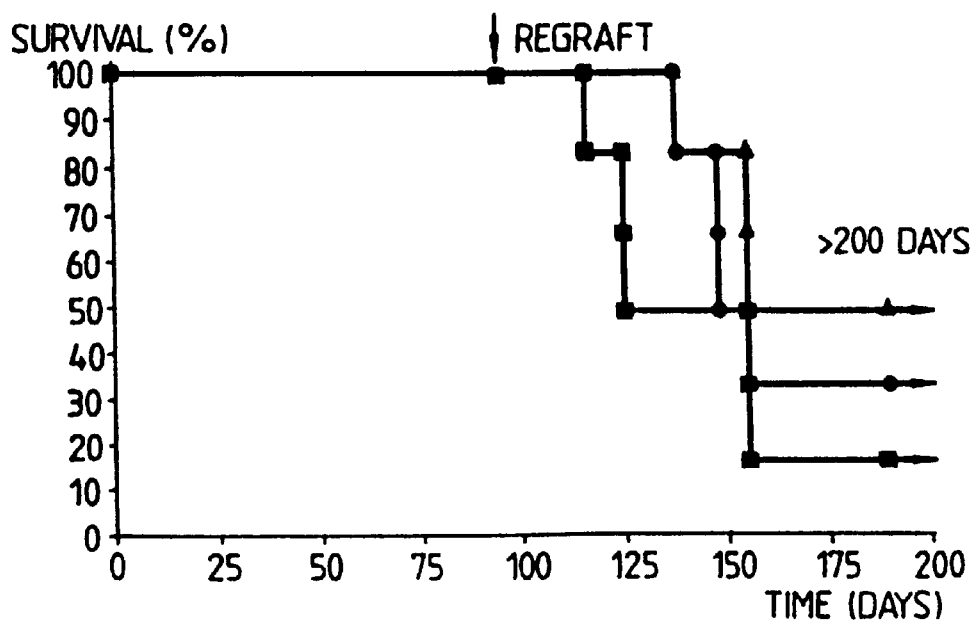

FIG. 10 shows the induction of tolerance to MHC-mismatched skin grafts. Groups of 8–12 CBA/Ca mice were grafted with B10 skin on day 0, and treated with monoclonal antibodies from day 0 to 21, as described in Example 2.

(a) The first group were control mice (▼) given no antibody. A second group (♦) were given only rat IgG$_{2a}$ antibodies, while the remaining group (●) all received the combined IgG$_{2b}$ and IgG$_{2a}$ protocol. This last group were given new B10 skin grafts (▲) and third party BALB/c skin (■) on day 119.

Analysis of graft survival: control (no antibody) group MST-14 days compared to IgG$_{2a}$ group MST=48 days P<0.001: Combined protocol original B10 grafts MST>250 days compared to second B10 grafts MST=44 days (from day 119) P<0.002: second B10 grafts compared to third party BALB/c grafts MST-13, P<0.003.

(b) A group of 8 CBA/Ca mice were given B10 skin grafts together with the combined IgG$_{2b}$ followed by IgG$_{2a}$ antibody protocol (●). The mice were given second B10 skin grafts on day 91 (▲) together with third party B10.BR skin (■).

Analysis of graft survival: all groups MST>200 days.

Figure 11:
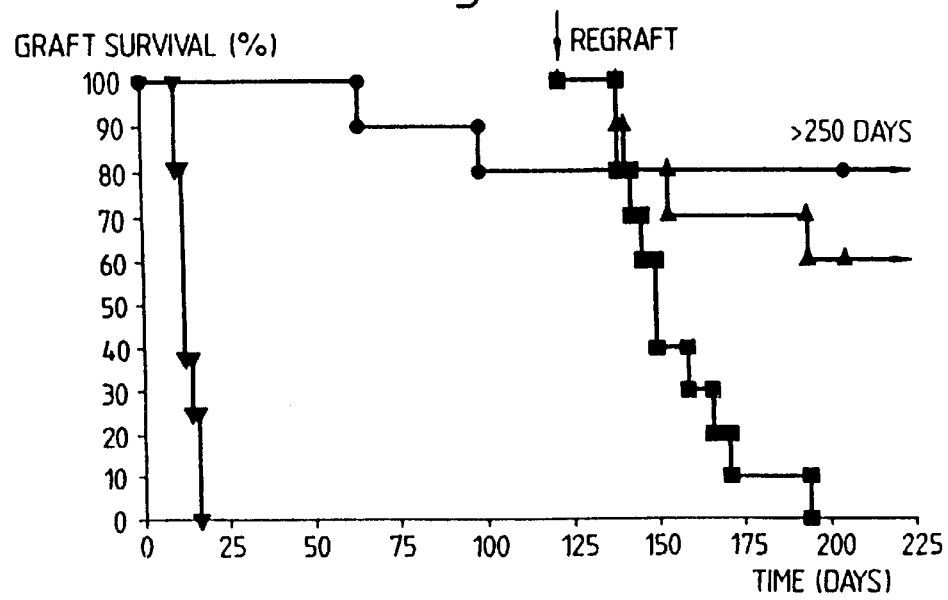

FIG. 11 shows the induction of tolerance to multiple minor antigen mismatched skin. Two groups 8 and 10 CBA/Ca mice were given AKR/J skin grafts on day 0. Control mice (▼) received no antibody. The remaining group were given the combined rat IgG$_{2b}$ followed by rat IgG$_{2a}$ antibody protocol (●), and were regrafted at day 122 with fresh AKR/J skin (▲) and third party minors different B10.BR skin (■).

Analysis of graft survival: no antibody controls MST=13 compared to combined protocol original AKR/J grafts MST>250 days, P<0.001: Second AKR/J grafts MST>128 days compared to third party B10.BR grafts MST-27 days, P<0.009.

FIG. 12 shows the induction of tolerance to multiple minor antigen mismatched skin in primed recipients. Recipient CBA/Ca mice were primed to donor minor antigens by ip injection with 10$^7$ irradiated (2000 rad) spleen cells from either AKR/J (a,b) or B10.BR (c,d), three weeks prior to skin grafting. Groups of 5–13 mice were grafted with AKR/J (a,b) or B10.BR (c,d) skin (●) under cover of monoclonal antibodies from day 0–21, as described in Example 2. Two groups received the combined IgG$_{2b}$ and IgG$_{2a}$ protocol (a,c), and two were given rat IgG$_{2a}$ antibodies only (b,d). Mice were regrafted on day 89 (a,c) or day 96 (b,d) with second donor-type (▲) grafts (AXR/J in groups a and b; B10.BR in groups c and d) and third party minors different (■) skin (B10.BR in groups a and b; AKR/J in groups c and d).

Analysis of graft survival: (a) combined protocol original AKR/J grafts MST>225 days compared to third party B10.BR grafts MST-41 days (from day 89), P<0.007. (b)IgG$_{2a}$ treated original AKR/J grafts MST>200 days compared to third party B10.BR grafts MST-42 days (from day 96), P<0.02. (c) all groups MST>day 225 of experiment (d) all groups MST>day 200 of experiment.

FIG. 13 shows the induction of tolerance in mice actively rejecting a first skin graft. Two groups of 6 and 11 CBA/Ca mice were grafted with AKR/J skin on day 0, without any monoclonal antibody treatment. On day 14, when roughly half the mice had rejected these first grafts (●), second AKR/J skin grafts were given in a fresh graft bed and monoclonal antibody treatment initiated (▲). Mice then received either the combined rat IgG$_{2b}$ followed by IgG$_{2a}$ three week protocol (a) or rat IgG$_{2a}$ antibodies alone (b).

Analysis of graft survival: (a) first AKR/J grafts MST=12 days compared to second, combined protocol treated AKR/J grafts MST>92 days, P<0.004. (b) second IgG$_{2a}$ treated AKR/J grafts MST>75 days, compared to all first grafts in (a) and (b) MST=12 days; P<0.003.

EXAMPLE 1

MATERIALS AND METHODS

Experimental Animals

CBA/Ca, B10.BR and BALD/c mice were bred and kept in the conventional animal facility in the Department of Pathology, University of Cambridge, and were used in age- and sex-matched groups.

Identification of Monoclonal Antibodies by Flow Cytometry

A rat T-cell line NB2-6TG (kindly provided by Dr. J. Howard) was transfected with the mouse CD4 gene (Gorman et al, PNAS USA 84, 7644, 1987). This line, NB2.L3T4.Hyg/2.1 was used to screen new CD4 mAbs from a rat anti-mouse thymocyte fusion. Cells (1–5×10$^6$) were incubated with test supernatants, followed by FITC-conjugated rabbit anti-rat Ig serum (Dako, Glostrup, Denmark). The fluorescence staining was analysed by flow cytometry on a Cytofluorograph (model 50-H Ortho, Westwood, Mass., USA) and data were processed by an Ortho 2150 computer.

For competitive binding of mAbs, L3T4/Hyg 2.1 cells were incubated firstly with biotinylated mAbs (1 μg/10$^5$ cells) on ice in the presence of 10 μg unlabelled mAbs for 30 minutes. Streptavidin-FITC (Amersham, U.K.) was added for a further incubation of 15 minutes. The results were analysed by the Ortho Cytofluorograph.

Two-colour fluorescence staining was carried out by serially incubating mouse spleen cells with biotinylated first mAb, streptavidin-phycoerythrin (Serotech, Kidlington, U.K.), second mAb and FITC-conjugated, isotype specific mAbs. The green and red fluorescence was detected and displayed on a log scale by the Ortho Cytofluorograph.

Immunofluorescence Staining of Peripheral Blood Lymphocytes (PBL)

Mouse PBL were separated by centrifugation on Ficoll (specific density 1.079, Phamacia, Sweden) at 3000×g for 20 minutes. Cells at the interface were collected and washed in PBS/BSA/azide. They were then stained either with rIgG$_{2b}$ mAbs in tissue culture supernatant, followed by FITC conjugated NORIG 7.16 (anti-rIgG$_{2b}$) or with biotinylated mAbs and followed by FITC-streptavidin (Amersham). The results were analysed by flow cytometry as above.

Complement Lysis

Complement lysis was performed as described previously. In brief, mAbs were diluted and incubated with $^{51}$Cr labelled mouse thymocytes and 2% guinea pig serum added as the complement source. After 45 minutes at 37° C., the supernatant was collected and radioactivity measured by a Philips Automatic Gamma Counter (Philips, Eindhoven, The Netherlands). The specific lysis was calculated as % of lysis=$(e-s)/(t-s)\times 100$, where e is the sample count, s is the spontaneous release and t is the total count.

Induction of Tolerance to Human Gamma Globulin (HGG)

The method of tolerance induction to HGG has been described previously (Benjamin et al, J. Exp. Med 163, 1539, 1986). Normal CBA/Ca mice were injected with CD4 mAbs intravenously (i.v.) on day 1, intraperitoneally (i.p.) on day 0 and 1. 1 mg of heat-aggregated HGG was given i.p. on day 0. The mice were re-challenged with 0.5 mg HGG on days 21 and 31. On day 38, the IgG anti-HGG response was measured by ELISA.

Detection of Mouse Antibody Responses by ELISA

To measure murine antibody responses, sample sera were serially diluted in flat-bottom flexible plates (Becton Dickinson, USA) coated with purified protein antigens and incubated for 30 minutes. The plates were washed with PBS/0.05% Tween 20 (Sigma, Poole, UK) and then incubated with biotinylated sheep anti-mouse IgG (Amersham) for 30 minutes, and washed as above. Streptavidin-horse radish peroxidase (Amersham) was added in the plates for 15 minutes and after another 3 washes, the reaction was developed by 5mg/ml o-phenolenediamine and 0.1% hydrogen peroxide. The absorbence at 490 nm was read and titres determined by comparison with a standard positive control.

Skin Transplantation

Skin grafts were transplanted by a modified method of Billingham et al (Nature 172, 603, 1953). Recipient mice were anaesthetised with 1 μg/mouse Hypnodil and 0.2 μg/mouse Sublimase (Janssen, Oxford, UK) via i.p. injection. Full-thickness skin graft from donor tail (0.5 cm×0.5 cm) was transplanted onto the graft bed on the lateral thoracic wall, covered with vaseline gauze, cotton bandage and protected by plaster for 7 days. The graft survival was observed and recorded daily thereafter, the end point of survival being the last day when no live graft tissue could be seen.

The median survival time (MST) was calculated and analysed by the Logrank method (Peto et al, Br. J. Cancer 35, 1, 1977). Mice were thymectomised at 4 weeks of age by the method of Monaco et al (J. Immunol, 96, 229, 1966) and used at least 4 weeks later. All were checked at sacrifice and none were found incompletely thymectomised.

Preparation of Bone Marrow Cells for Transplantation

Bone marrow cells were harvested from donor mice pretreated with CD4 and CD8 depleting antibodies to remove T-cells. $2 \times 10^7$ live cells were transferred into suitably prepared recipients to determine whether tolerance could be induced. Chimerism could be determined by measurement of donor Ig allotype or donor Thy-1.1 allotype as described previously (Qin et al, 1989, J.Exp. Med. 169, 779).

Adoptive Transfer of Spleen Cells

Donor spleen cells were obtained from either naive CBA/Ca mice or CBA/Ca mice that had been presensitized to B10.BR spleen cells and skin grafts 4–8 weeks previously. These were transferred into tolerant CBA/Ca recipients that had been treated with mAbs, grafted with B10.BR skin and had carried the grafts for more than 200 days. Each recipient mouse was injected intravenously with $5 \times 10^7$ spleen cells. As controls, adult thymectomised (ATx) mice were treated with $rIgG_{2b}$ CD4 and CD8 mAbs to deplete CD4+ and CD8+ cells. Such mice are unable to reject allogeneic grafts (Cobbold et al, 1984, Nature, 312, 548) and were used here to demonstrate that the transferred cells could function.

Mixed Lymphocyte Culture

Responder spleen cells were washed and resuspended in Iscove's modified Dulbecco medium (IMDM) supplemented with 10% heat-inactivated human AB serum. Stimulator spleen cells were treated with 25 μg/ml mitomycin-C (Sigma, Poole, U.K.) at 37° C. for 30 minutes and washed twice in IMDM. $3 \times 10^5$ responder cells and $3 \times 10^5$ stimulators were cultured in 96-well flat-bottom microtitre plates at 37° C. with 5% $Co_2$. On day-4, cells were pulsed with 10 μCi/ml $^{125}$iodo-deoxyuridine (Amersham) for six hours. Incorporation was measured in a gamma counter. Geometric means of triplicates were calculated.

Stimulation of Lymphocytes with Monoclonal Antibodies

The mitogenic anti-Vβ6 m, 46-6B5 was kindly given by Dr. H. Hengartner (Payne et al, 1988, PNAS USA 85, 7695). The mAb was coupled onto 96-well flat-bottom plates at 1 μg/ml at 37° C. overnight, then rinsed extensively with IMDM before use. The CD3 mAb, 145-2C11, was a kind gift from Dr. J. Bluestone (Leo et al, 1987, PNAS USA 84, 1374), and was used at 1:100 dilution of serum-free tissue culture supernatant. $4.5 \times 10^5$ spleen cells were added into each well, in IMDM and 10% heat-inactivated human AB serum. Proliferation after 4 days of culture was measured as above.

RESULTS

Identification of $rIgG_{2a}$ mAb Binding to CD4 Molecule

A mAb, YTS 177.9, was isolated on the basis of its binding to an L3T4 transfected cell line using immunofluorescence staining (Table 1). Its isotype was determined by reaction with an anti-$rIgG_{2a}$ mAb, RG 7/1.7 (Springer et al, Hybridoma 1,257, 1982) by ELISA (data not shown). Further analyses were carried out to compare this mAb with two other CD4 mAbs described previously. Binding inhibition studies showed that YTS 177.9 bound to the same epitope as YTS 191.1 (Cobbold et Al, 1984, Nature 312, 548) and GK 1.5 (Dialyras et al, Imm. Rev. 74, 29–56, 1983) (both CD4 mAbs) but different to that bound by another CD4 mAb YTA 3.1 (Qin e Al, Eur. J. Immunol, 17, 1159, 1987) which recognises a separate epitope. In two-colour flow cytometry, YTS 177.9 and YTA 3.1 stained the same population of mouse spleen cells, which is distinct from those stained by a CD8 mAb, YTS 169.4 (Cobbold et al, 1984, Nature 312, 548).

Figure 1B:
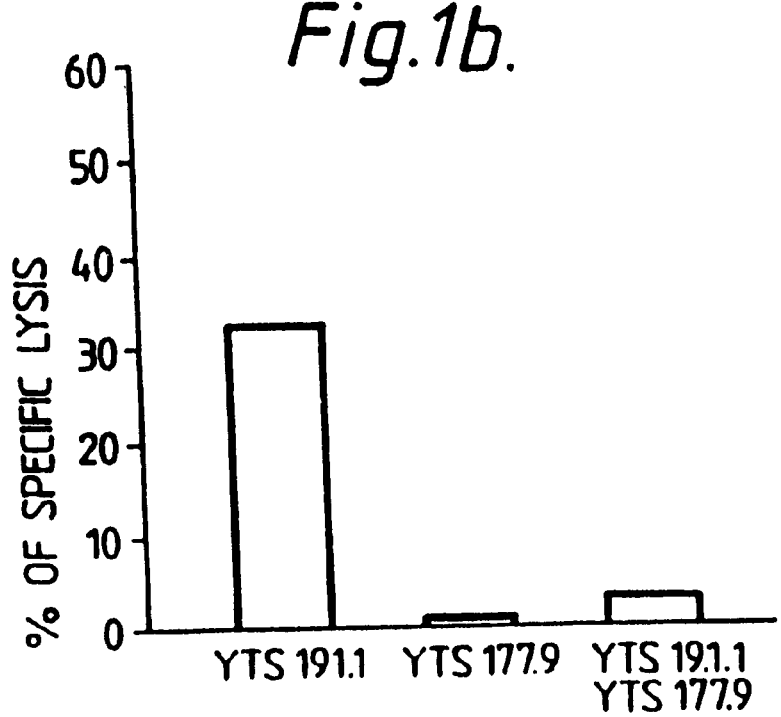

The specificity of YTS 177.9 was also tested by specific $^{51}$-Cr release assay. Although the mAb was inefficient at lysis when used alone, it exhibited synergy with the CD4 mAb YTA 3.1. (FIG. 1a). On the other hand, YTS 177.9 interfered with the lysis mediated by $rIgG_{2b}$ mAb YTS 191.1 which in fluorescence staining was shown to be cross-inhibitory (FIG. 1b).

The rIg2a CD4 mAb Does Not Deplete T cells in vivo

To determine the effect of the rIgG2a CD4 mAb on in vivo cell depletion, we used adult thymectomised (ATX) mice because in these animals, T-cell recovery following mAb depletion is much less efficient than in normal mice, due to the absence of thymus-dependent T-cell regeneration. By monitoring the change of peripheral T cells after mAb injection, it was possible to distinguish true depletion from temporary antigenic modulation or lymphocyte re-distribution. Each mouse received 2 mg of either IgG2a or IgG2b antibodies and peripheral blood lymphocytes were analyzed by flow cytometry before and at various times after treatment. As can be seen in FIG. 2, one week after completion of the IgG2b mAb therapy, about 90% of the CD4+ cells were depleted from the periphery. This was accompanied by a decreased percentage of total T cells and a slight increase of CD8+ cells. In contrast, although the IgG2a mAb treatment reduced the percentage of CD4+ cells, the total percentage of Thy-1+ cells did not change significantly, nor did that of CD8+ cells. This is considered to be the result of antigenic modulation of CD4 molecules following antibody binding. Four weeks after treatment, the T-cell numbers in IgG2b treated groups still remained low, whilst the YTS 177.9 treated group showed a normal level of CD4+ cells.

Induction of Tolerance to HGG under Cover of rIgG2a CD4 mAb

Previous work using CD4 F(ab')$_2$ mAb fragments has suggested that mAb facilitated tolerance to protein antigens may not need the depletion of CD4+ T-cells. In the present study, we investigated if the non-depleting CD4 mAb, like F(ab')$_2$ fragments, could have the same effect. Mice were given YTS 177.9 or YTS 191.1 in a 3-day course and one injection of HGG (0.5 mg/mouse) on the second day (Day 0). When re-challenged with HGG 4 weeks later, YTS 191.1 treated mice and mice given high dose (1 mg/mouse) of YTS 177.9 had become tolerant to HGG (FIG. ). However, mice that had received 0.1 mg or less of the mAb were still able to respond to HGG.

The Ability of YTS 177.9 to Induce Tolerance to rIgG2a mAbs

In vivo administration of xenogeneic antibodies usually elicits antiglobulin responses in the host. One of the features of CD4 mAbs is their ability to suppress this antiglobulin response and even to induce tolerance to other antibodies of the same isotype. In the present study, it was found that the rIgG2a CD4 mAb YTS 177.9 had the same property.

Mice given 0.1–1 mg/mouse YTS 177.9 made no primary antiglobulin response, (titre: <1:20). However, mice given 0.01 mg/mouse YTS 177.9 did mount a weak response (1:160). Six weeks after the first antibody injection, these animals were rechallenged with 'irrelevant' (rat anti-human) rIgG2a and rIgG2b mAbs, in Freund's adjuvant to ensure adequate stimulation. The rIgG2a was YTH 34.5 which is a mAb to human CDw52 (Waldmann et al, 1985, Adv. Exp. Med. Biol. 186, 869). The rIgG2b was YTH 12.5 which is a mAb to human CD3 (Waldmann et al, 1985). Mice were bled 4 weeks later and their serum anti-rat Ig titres were measured by ELISA. Just as rIgG2b mAbs rendered mice tolerant to rIgG2b immunoglobulins, mice given a high dose of YTS 177.9 (1 mg) were shown to have become completely tolerant to rIgG2a even after repeated boosts (FIG. 4). 0.1 mg YTS 177.9 was insufficient to induce tolerance although it had been immunosuppressive for primary responses. Mice given 0.01 mg YTS 177.9 or non-treated control showed secondary-type antiglobulin responses. Tolerance so induced was specific, as YTS 177.9 treated mice were still able to respond to rIgG2b immunoglobulin, while YTS 191.1 tolerant mice could still respond to rIgG2a.

Delay of Allograft Rejection by rIgG2a mAb Treatment

We found YTS 177.9 as effective as rIgG2b CD4 mAbs in its ability to prolong allogeneic skin graft survival after a short course of treatment. In the first experiment, normal CBA/Ca mice were given daily injections of either rIgG2a (YTS 177.9) or rIgG2b (YTS 191.1) for 2 weeks, starting from 3 days before allogeneic (BALB/c) skin transplantation (approx. 7 mg/mouse total mAb). In YTS 177.9 treated group, the MST was significantly prolonged to 20 days (untreated control: 11.3 days; $p \leq 0.05$, Table 2). This extended graft survival is very similar to that achieved by rIgG2b CD4 mAb which depleted cells (MST 19 days).

In graft rejection across MHC Class I and II mismatches, the depletion of both $CD4^+$ and $CD8^+$ subsets has been shown to significantly improve the graft survival beyond the effects of CD4 mAbs alone (Cobbold e al, Transplantation, 42, 239, 1986). In the present study, we used another rIgG2a CD8 mAb, which also had little effect on in vivo cell depletion together with the rIgG2a CD4 mAb. This CD8 mAb, YTS 105.18 was found to synergise with the rIgG2a CD4 mAb, YTS 177.9 in further prolonging fully allogeneic skin graft survival. For the purpose of comparison, equal amount of two rIgG2b mAbs (YTS 191.1 and YTS 169.4) or the two rIgG2a mAbs were administered. A total of 3mg/mouse of the mAbs were given on days 0, 2 and 4 relative to skin grafting. The rIgG2b treated CBA/Ca mice rejected BALB/c skin with the MST of 24 days (versus control of 10.5 days, $p \leq 0.005$, FIG. 5). Surprisingly, the graft survival in the group treated with rIgG2a CD4 and CD8 mAbs was even longer than that of mice treated with rIgG2b mAbs. 3 out of 4 rIgG2a-treated CBA mice did not reject their BALB/c skin grafts until 45 days after transplantation (MST 46.5 days; versus IgG2b treated group, p<0.03).

Tolerance to Skin Allografts

Although there have been reports documenting the permanent survival of certain allografts such as heart or pancreas after CD4 mAb treatment, it has been generally found more difficult to maintain a long-term skin graft with mAb treatment alone. We have previously shown that treatment with CD4 depleting mAbs allowed the acceptance of multiple minor mismatched bone marrow, and such mice were then tolerant of donor skin. In the present study, we grafted CBA/Ca mice with skin from B10.BR mice and treated the recipients with YTS 177.9 (CD4) and YTS 105.18 (CD8). In this H-2 compatible, multi-minor transplantation antigen mismatched combination, all the mice given a 3-week course of mAb treatment accepted the first skin for 90 days. At this time, a second donor-type skin, together with a third party (B10.D2) graft was transplanted. The data in FIG. 6 shows that the first and second grafts all continued to survive indefinitely (>90+ days) while the B10.D2 skin was rejected promptly. Of the mice that had been given only 2 injections of the mAbs, 3 of 6 maintained the B10.BR skin for 90 days but these were slowly rejected after the second skin graft.

Tolerance and Anergy in Mice Grafted with Multiple Minor Antigen Mismatched Bone Marrow Injection of CBA/Ca mice with the combination of rIgG2a CD4 and CD8 mAbs permitted bone marrow engraftment and tolerance to B10.BR skin (FIG. 7). A similar protocol also permitted chimerism and tolerance by AKR/J marrow (MIs-$1^a$) (FIG. 7). As tolerance could be achieved without depletion of CD4 cells we had the opportunity to follow the fate of Vβ$6^+$ CBA/Ca T-cells in the periphery of the recipient. 4 weeks after monoclonal antibody and marrow infusion the spleen cells of these animals were unable to respond to MIs-$1^a$ in vitro and were poorly reactive to solid phase stimulation with a mitogenic Vβ6 mAb (Table 3). FACS analysis showed normal numbers of Vβ$6^+$ cells in the periphery (these were shown to be of recipient Thy1.2 allotype). Clearly the Vβ$6^+$ T-cells were anergic to stimulation. As the CD4 mAb does not deplete T-cells these were assumed to be peripheral T-cells that had been energized.

To confirm that the thymus was not essential for tolerance of peripheral T-cells AXR/J bone marrow was again used, this time to tolerise ATx mice to MIs-$1^a$. Again the spleen T-cells became anergic to MIs-$1^a$ and Vβ6 stimulation (Table 4). Neither the bone marrow nor the antibody alone could reproduce this. Clearly the combination of antibodies and marrow were required to bring about peripheral T-cell anergy.

The Demonstration of Peripheral Tolerance to Skin Allografts in Adult Thymectomised Mice To confirm that we were looking at bone-fide peripheral tolerance induced by the skin grafts, we repeated the experiment in ATx mice. As the rIgG2a mAbs do not kill T-cells, we expected that immune functions in these mice should return to normal soon after the cessation of antibody therapy. As was found in euthymic mice, tolerance was induced to the test skin, and third party grafts were rejected promptly (FIG. 8).

The "Peripheral" Tolerant State is Refractory to Infusion of Normal Lymphocytes In both the above skin allograft tolerant models, we asked whether the adoptive transfer of normal lymphocytes could terminate the tolerant state. 50 million spleen cells transfused from normal donors could not restore the ability to reject in either case. A perennial problem with this type of experiment is to show that the infused cells survive and function. In part this was controlled for by transferring the same number of spleen cells into T-depleted ATx mice. In this case the transferred cells were able to mediate skin graft rejection. Only "primed cells" transferred into tolerant mice could break the tolerant state (Table 5). Similar results were found in the mice tolerant to HGG, where tolerance could not be broken by adoptive transfer of normal cells unless recipient CD4+ T-cells had been depleted first. Whatever the difficulties of controlling such experiments, we must conclude that the immune system of tolerant animals does not allow normal virgin T-cells to express their immune potential.

EXAMPLE 2

MATERIALS AND METHODS

Mice

CBA/Ca, C57Bl.10/Pc, BALD/c, B10.BR and AKR/J mice were bred and maintained in the conventional animal facility of the Department of Pathology, University of Cambridge. Sex matched groups of mice were used at 6–12 weeks of age.

Monoclonal Antibodies

All the rat monoclonal antibodies used in these experiments are listed in Table 1. Antibodies were prepared from ascitic fluid produced in Pristane-primed (DAxLOU)F$_1$ rats by precipitation with 50% saturated ammonium sulphate followed by dialysis into phosphate buffered saline (PBS;pH7.2). The protein concentration was adjusted to 10 mg/ml as estimated by OD$_{280}$ containing 2–5mg/ml of monoclonal antibody. All antibody preparations were passed through a 0.2 micron filter before administration to mice.

Skin Grafting

Skin grafts were performed as previously reported (Cobbold et al, 1986, Transplantation, 41, 634). In brief, donor tail skin grafts (0.5 cm to 1.0 cm square) were transplanted onto the lateral thoracic wall of recipient mice under anaesthesia. The grafts were covered with gauze and plaster bandage for 7 days. Graft status was documented three times per week for the first month, and approximately weekly thereafter. Differences in survival were analyzed using the Log-Rank method (Peto et al, 1977, Br. J. Cancer, 35, 1). When performing multiple re-grafts from a range of donors, these were transplanted into a single prepared graft bed, usually on the opposite flank to the original skin graft (Cobbold et al, 1986, Nature, 323, 164). Grafts were observed three times per week initially, and weekly thereafter. Median graft survival times (MST) are given as the number of days until rejection is complete, but tolerated grafts with indefinite survival times were generally in good condition with normal hair growth.

Induction of Tolerance to Skin Grafts

Skin grafts were used as the only source of antigen/tolerogen, and were performed as described above, on the same day as the start of monoclonal antibody treatment. Monoclonal antibodies were administered three times per week from day 0 to day 21 (inclusive), with the first two injections (day 0 and day 2) intravenous, and the remainder intra-peritoneal. The total dose of all antibodies given per injection was 2mg of ascitic immunoglobulin fraction in 0.2 ml of PBS. For rat IgG2b antibodies this was 0.5 mg each of YTS 191.1.2, YTA 3.1.2, YTS 169.4.2 and YTS 156.7.7 (a synergistic depleting cocktail of CD4 and CD8 monoclonal antibodies; (Qin et al, 1987, Eur. J. Immunol. 17, 1159). In the case of rat IgG2a antibodies, 1 mg each of YTS 177.9.6 (CD4) and YTS 105.18.10 (CD8) were used. For the combined depletion and blocking protocol, the synergistic rat IgG2b cocktail was given i.v. on days 0 and 2 and the rat IgG2a CD4 and CD8 three times per week thereafter i.p. until day 21.

Levels of Active Monoclonal Antibody in Serum

Serum samples taken from individual mice at various times during and after monoclonal antibody administration were added, 25 μl at ⅕ dilution in PBS containing 1% w/v bovine serum albumin (BSA) plus 5% v/v heat inactivated normal rabbit serum, to 5×10$^5$ CD4 or CD8 transfected cells. The CD4 transfectant was the rat NB2-6TG line expressing mouse L3/T4 (Example 1) while the CD8 (Lyt-2) gene was expressed at high levels in mouse L-cells (Zamoyska, 1985, Cell, 43, 153). Bound antibody was detected using monoclonal anti-rat IgG2a coupled to FITC (MARG2A-FITC; Serotec, Oxford, UK) at the manufacturer's recommended dilution, and analysis was on an Ortho 50H Cytofluorograf with 1250 computer (Ortho, Westwood, Mass., USA). The mean fluorescence was compared to a standard dilution series of purified CD4 or CD8 antibody (YTS 177.9.6 or YTS 105.18.10) in normal mouse serum to derive equivalent concentration values for the serum samples. Where the fluorescence showed saturating antibody, or no detectable fluorescence above background, the result was assumed to be greater than or less than the titratable range of the standard curve.

Preparation of Peripheral Blood Leucocytes

Mice were bled individually from the tail vein (approx. 0.1 ml) into sterile tubes containing 1 U heparin. The plasma was then removed after centrifugation in a microfuge (6000 rpm) for 2 mins. Red blood cells were lysed twice by adding 0.9 ml of water for 10 secs at room temperature followed by 0.1 ml of 10× phosphate buffered saline and the white cells collected by centrifugation at 1,000 rpm for 7 mins (Chandler et al, 1979, J. Immunol. Methods 31, 341).

Monitoring T-cell Subsets for Depletion

Peripheral blood leucocytes were prepared from individual treated mice as described above. These were stained with supernatants containing monoclonal antibodies against either CD4 (YTS 191.1.2 plus YTA 3.1.2) or CD8 (YTS 169.4.2 plus YTS 156.7.7) antigens. Other monoclonal antibodies (see Table 6) were also used as controls. Bound antibody was detected using a mixture of monoclonal anti-rat IgG2b-FITC (NORIG-7.16-FITC; Clark, 1986, Methods Enzymol. 121, 548) and monoclonal anti-rat kappa light chain (MAR-18.5-FITC; Lanier et al, 1982, Hybridoma, 1, 125). The fluorescence was analyzed using an Ortho 50H Cytofluorograf with 1250 computer and linear amplifiers, with gating on forward and ninety degree scatters to select for live lymphocytes.

Mixed Lymphocyte Cultures

Responder cells were obtained from individual mouse blood samples (approx 0.2 ml) by water lysis as described above. Each sample was assayed for proliferation by splitting the cells into three U-bottom tissue culture microtitre wells (approx 4×10$^5$ white cells per well) containing 4×10$^5$ well washed, mitomycin-C (Sigma, Poole, UK; 25 μg/ml)

treated stimulator spleen cells. The final volume of Iscove's modified Dulbecco's medium (IMDM) containing 10% heat inactivated human AB serum was 0.1 ml. After 3 days at 37° C. in a 5% $CO_2$ gassed incubator, 5 μl of $^{125}$I-deoxyuridine (IUDR; 10 μCi/ml, Amersham, UK) was added for six hours. The 125I incorporation was measured by harvesting the cells onto glass fibre filters and counting on a Philips Automatic Gamma Counter.

A Combination of Depleting and Blocking CD4 and CD8 Antibodies is Permissive for Tolerance to MHC-Mismatched Skin Grafts Example 1 has shown that three weeks of therapy with non-depleting CD4 and CD8 antibodies permitted tolerance to multiple minor incompatible skin grafts. In order to establish a treatment protocol that might tolerize across strong MHC differences we compared the effects of administering depleting (rat IgG2b), non-depleting (blocking rat IgG2a) and a combination of depleting followed by blocking CD4 and CD8 antibodies to CBA/Ca (H-2k) mice grafted with BALB/c (H-$2^d$) skin (FIG. 9). As we have previously reported, a strictly depleting protocol delayed rejection significantly, but all mice rejected within 70 days (MST=55 days). Non-depleting antibodies were here less effective (MST=28 days), but a combination of two depleting doses followed by blockade with rat IgG2a antibodies gave the longest graft survival (MST>100 days), although most (but not all) grafts were rejected by 200 days. In this experiment, second BALB/c test grafts were given at day 94, together with third party B10 (H-$2^b$) skin. These third party grafts were rejected promptly (MST=16 days), demonstrating that the mice had returned to immunocompetance, whilst the second BALB/c grafts survived for a median of 43 days. This shows that there must have been some degree of specific unresponsiveness to BALB/c graft antigens.

Although we did not obtain complete tolerance in this strain combination, we found the same combined protocol to be fully tolerance permissive when B10 (H-$2^b$) skin was grafted onto MHC incompatible CBA/Ca (H-$2^k$) mice. FIG. 10 shows that ⅝ recipient mice kept their original skin grafts indefinitely (>250 days), while all mice rejected the third party BALB/c skin grafted on day 119 within 15 days. Second B10 grafts had substantially extended survival times (MST=44 days), but all were eventually rejected even when the first grafts, assumed to be genetically identical, were maintained. This result is reproducible and shows clearly that the tolerated first graft enjoys privilege of tenure, despite the presence of effector cells capable of rejecting the second graft. Whatever the mechanism, the original skin graft must have induced, and maintained, a state of unresponsiveness to itself. The ability of mice to distinguish between the first and second B10 grafts seemed to be dependant on rejection of the third party skin, as ⅝ mice given B10.BR instead of BALB/c grafts remained tolerant to all three (FIG. 10). This demonstrates that the recipients were tolerant of B10 minor antigens in the context of both donor MHC, which means that the graft can itself present for tolerance, and also recipient-type MHC, which must have been through reprocessing of the original graft antigens and presentation for tolerance by recipient APCs.

This is the first report of antibody mediated tolerance across complete MHC barriers using highly immunogenic skin grafts as the only source of tolerogen. It should be stressed that the graft itself must have provided all the antigen presentation necessary for tolerance to occur.

The Combination of Depleting and Blocking Antibodies Also Permits Tolerance to Skin Matched for MHC but Mismatched for Multiple Non-MHC Minor Antigens In Example 1 we have demonstrated that blocking with monoclonal antibodies to CD4 and CD8 was sufficient to obtain tolerance to skin grafts differing in multiple minor antigens (B10.BR onto CBA/Ca). In FIG. 11 it can be seen that the combined depleting followed by blocking protocol was also effective with 8/10 CBA/Ca mice keeping their AKR/J grafts indefinitely. Six of these mice also held second AXR/J grafts (skin grafted at day 122 without further antibody therapy), while all mice rejected third party minor mismatched skin (B10.BR). The rejection of this third party skin was, however, somewhat slower than normal CBA controls (27 days compared with the normal 14; Cobbold et al, 1986, Transplantation, 41, 634). The reverse combination (B10.BR onto CBA/Ca) was also rendered tolerant using the depletion followed by blocking protocol (⅘ grafts >220 days), but ⅖ mice accepted both the third party minors difference AKR/J skin as well as the second B10.BR graft (data not shown). This presumably reflects the large number of shared minor antigens and is reminiscent of the finding of "dominant" tolerance seen in a different experimental model (Zamoyska et al, 1989, Eur. J. Immunol. 19, 111).

In summary for this section, we wish to conclude that CD4 and CD8 antibodies, when used appropriately, permit tolerance to be induced across both MHC and non-MHC antigen differences, to skin grafts alone, without the need for any further haemopoietic source of antigen, nor other myeloablative therapy. Clearly, skin grafts are able to present antigen directly to peripheral T-cells either for activation, which leads to rejection, or for inactivation, which instead lead to acceptance and tolerance.

The Effects of Combined Rat IgG2b and IgG2b Antibodies on Circulating T-cells In view of the remarkable tolerogenic effects seen in the above experiments, it was important to assess the effects of the monoclonal antibodies on circulating $CD4^+$ and $CD8^+$ T-cells. We have shown previously that rat IgG2b antibodies to either CD4 or CD8 deplete their target T-cells (Cobbold et al, 1984, Nature, 312, 548). In Example 1 rat IgG2a antibodies, in the doses given, tended only to modulate the antigen from the cell surface. In the case of the combined protocol, the initial doses of rat IgG2b CD4 and CD8 monoclonal antibodies caused a reduction in the number of T-cells as expected, and then the proportion of $CD4^+$ and $CD8^+$ cells actually started to recover during the continued treatment with IgG2a antibodies (Table 7), although the amount of antigen expressed was much reduced (data not shown). Residual antibody was present on the T-cells throughout the administration period, making detailed measurements of $CD4^+$ and $CD8^+$ cells difficult. Thereafter, the proportion of T-cells in the peripheral blood remained diminished for at least one month after stopping the antibody, an effect not observed when IgG2a antibodies were given alone in equivalent does (data not shown).

One mechanism for the suppression of graft rejection by non-depleting monoclonal antibodies is through blocking the function of CD4 and CD8 accessory molecules on the T-cell surface during antigen presentation. This would be most effective only if serum antibody was maintained at levels sufficient to saturate antigen positive cells. The levels of active antibody in treated mice was indeed found to be sufficient to saturate the target CD4 and CD8 antigens throughout the three weeks of treatment, and in some mice up to three weeks after stopping antibody administration (Table 8). However, by day 60, there was no detectable (<0.5 ng/ml CD4 and <10 ng/ml CD8) monoclonal antibody left in the serum which could otherwise have maintained a non-specific immunosuppression. It should be noted that none of the mice made any detectable antiglobulin (neither anti-species nor anti-idiotype) as measured by a capture ELISA, indicating that mice were also rendered tolerant of rat imunoglobulin by this protocol.

Tolerant Mice Can Still Respond In Vitro

We found that CBA mice rendered tolerant of B10 skin as described above were still capable of proliferating in vitro to B10 stimulator spleen cells (Table 9), showing that a significant number of allo-reactive T-cells had not been deleted. Clearly the recipients immune system is tolerant to the antigens presented by the original graft, but is still capable of reacting to in vitro presentation by spleen stimulator cells or a second skin graft.

The Induction of Tolerance in Mice Previously Primed To Minor Antigens

Given that virgin T-cells in the peripheral immune system could be tolerized by graft-born antigens, we sought to determine if primed T-cells were also tolerance susceptible. We found that both of the two treatment protocols (blocking alone, or depletion followed by blocking) were effective for the induction of tolerance to either AKR/J or B10.BR skin in CBA/Ca mice previously primed with irradiated donor spleen cells (FIGS. 12a–12d). In contrast, we have previously shown that depleting the CD4$^+$ and CD8$^+$ T-cells, although equally immunosuppressive in naive or primed mice, was not tolerance permissive for multiple minor antigen mismatched skin, as all the grafts were eventually rejected (Cobbold et al, 1986, Transplantation, 41, 634).

The only difference between the naive mice of FIG. 11 and the primed mice of FIG. 12 was seen after rechallenge. About half the mice in the group which had been primed and tolerized to AKR/J eventually rejected both first and second AKR/J grafts, although more slowly than the B10.BR third party grafts (MST=63 and 21 days respectively; FIG. 12a). In the B10.BR onto CBA combination the majority of mice held the original grafts indefinitely, while, in some mice, both the second B10.BR and AKR/J grafts rejected slowly (FIG. 12c). This difference in behaviour of the strain combinations is compatible with that seen in naive mice (see FIG. 11) and probably lies in the complex pattern of shared and unique minor antigens.

Tolerance Induction During Active Rejection of a Skin Graft

Figure 13A:
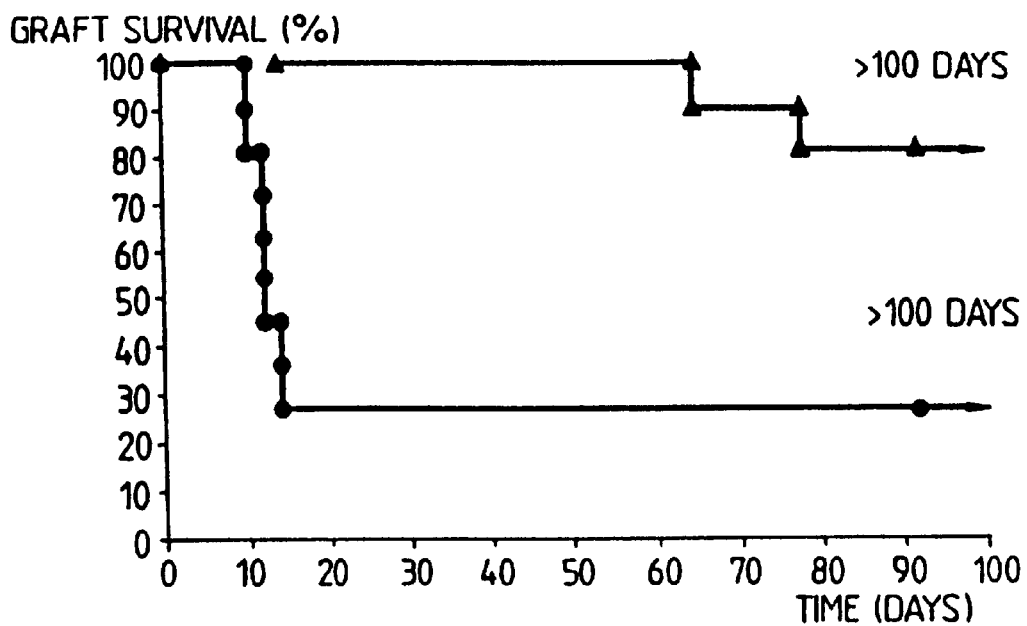
Figure 13B:
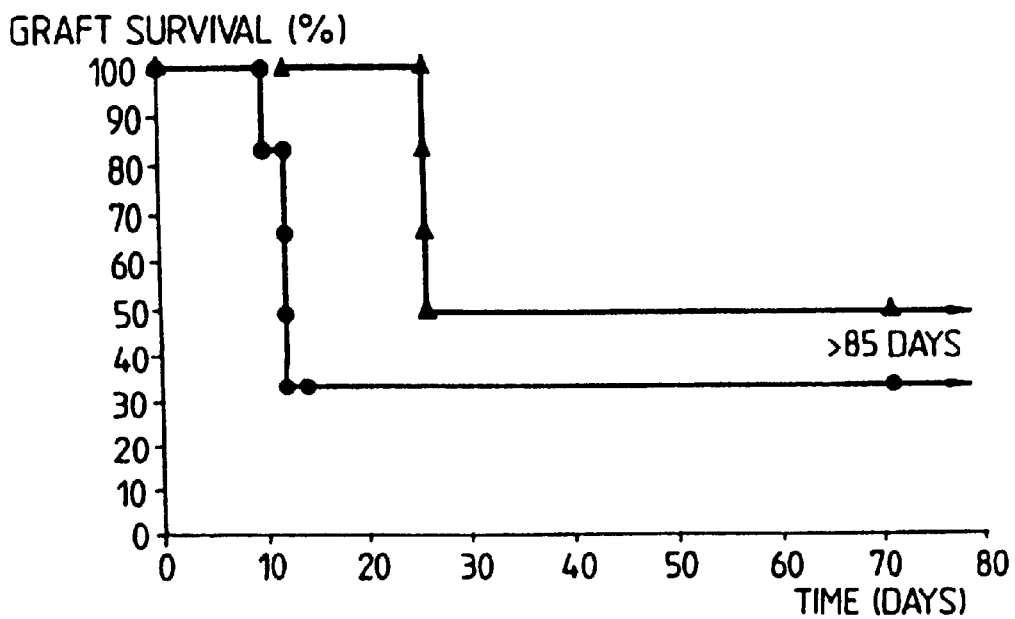

The finding that even sensitized T-cells are tolerizable has obvious clinical implications. It would clearly be advantageous to induce tolerance in the face of an ongoing immune response, especially in autoimmunity or during an organ rejection crisis after transplantation. In FIG. 13 it can be seen that it is indeed possible to reverse ongoing rejection of multiple minor antigen mismatched skin grafts and establish long-term survival, in some cases in both the first and second grafts. In this experiment, combined depletion followed by blockade was most effective (FIG. 13a), but as 3/6 of the mice given the blocking (non-depleting) antibodies also held their second grafts (FIG. 13b), it must be possible even for effector T-cells to be rendered inactive or tolerant.

TABLE 1

Binding of YTS 177.9 on L3T4 transfected cells

| Mab | % of positive cells L3T4[a] |
|---|---|
| YTS 177.9[b] | 98.7 |
| YTS 191.1[b] | 99.1 |
| YTS 177.9[c] and YTS 191.1 | 1.1 |
| YTS 177.9[c] and YTS 3.1 | 98.1 |

[a]L3/T4 transfected cell lines stained with respective Mabs and analysed by flow cytometry.
[b]Mabs were used as tissue culture supernatant followed by FITC conjugated rabbit anti-rat Ig.
[c]Biotinylated Mabs, which were incubated with excess amount of 'cold' Mabs given underneath. The fluorescence was developed with FITC-strepavidin.

TABLE 2

Delay of skin graft rejection by IgG2a and IgG2b CD4 Mabs

| MAB TREAT- MENT[a] | % OF CELLS[b] | | | GRAFT SURVIVAL (DAYS) | |
|---|---|---|---|---|---|
| | CD4$^+$ | CD8$^+$ | Thy-1$^+$ | B10.BR | BALB/c |
| YTS 191.1 | 1.9 ± 1.5 | 17.3 ± 1.7 | 20.2 ± 4.4 | 28,29,32, 58,65. | |
| YTS 191.1 | 1.2 ± 1.1 | 18.1 ± 2.3 | 24.5 ± 3.6 | | 15,18,19, 19,20,21. |
| YTS 177.9 | 28.3 ± 9.8 | 15.3 ± 0.4 | 48.8 ± 5.0 | 15,20,22, >120, >120, >120. | |
| YTS 177.9 | 27.5 ± 10.1 | 16.1 ± 1.2 | 46.9 ± 4.2 | | 19,19,20, 20,21,21. |
| none | 39.8 ± 3.0 | 12.5 ± 1.5 | 47.0 ± 2.8 | 10,11,12 12,13. | 9,10,10, 11,12,12. |

[a]Normal CBA/Ca mice were given CD4 Mabs for 2 weeks (appr. 7 mg/mouse) starting from 3 days before skin grafting.
[b]Peripheral blood collected 4 days after the last Mab injection were stained with biotinylated YTA 3.1 (CD4), YTS 156.7 (CD8) and YTS 154.7 (Thy-1), followed by streptavidin FITC. The results were analysed by flow cytometry.
[c]MST of B10.BR grafts: non-treated control: 12 days; YTS 191.1 treated: 32 days (v.s. control: p < 0.005).
YTS 177 treated: 22 days (v.s control p < 0.004, v.s YTS 191.1 group, p ≦ 0.7).
MST of BALB/c grafts: non-treated control: 10.5 days; YTS 191.1 treated 19 days (v.s. control, p ≦ 0.006);
YTS 171.9 treated: 20 days (v.s. control p ≦ 0.006, v.s. YTS 191.1 group, p ≦ 0.4).

TABLE 3

Tolerance of MIs-1[b] mice to MIs-1[a] antigen is associated with aneray of Vβ6+ cells

| | RESPONSES To: (cpm) | | | | % Vβ6+ |
|---|---|---|---|---|---|
| MICE | AKR/J | BALB/c | anti-Vβ6 | CD3 | -ve | cells |
| 1 | 772 | 11117 | 583 | 12350 | 596 | 10.2 |
| 2 | 439 | 8964 | 1173 | 9879 | 460 | 12.1 |
| 3 | 961 | 6498 | 1050 | 7719 | 703 | 8.7 |
| 4 | 1203 | 12866 | 1163 | 13496 | 1082 | 7.5 |
| 5 | 859 | 10784 | 764 | 11230 | 977 | 7.8 |
| Normal mice | 20756 | 9633 | 10440 | 11980 | 868 | 7.0 |
| | 27529 | 17253 | 10530 | 13291 | 642 | 10.2 |
| Marrow only | 38264 | 10042 | 13950 | 19087 | 815 | 8.1 |
| | 15832 | 8679 | 7267 | 13563 | 976 | 9.0 |

TABLE 4

Tolerance and anergy to MIs-1[a] in ATx MIs-1[b] mice[a]

| MICE | RESPONSES TO: (cpm)[b] | | | % Vβ6+ cells[c] |
|---|---|---|---|---|
| | AKR | BALB/c | Anti-Vβ6 | |
| 1 | 1348 | 8081 | 696 | 2.8 |
| 2 | 1145 | 10231 | 812 | 2.9 |
| 3 | 998 | 7311 | 976 | 3.7 |
| 4 | 1039 | 6508 | 793 | 3.3 |
| Control[d] | 12463 | 10283 | 7374 | 3.8 |
| Mice | 15578 | 8864 | 5824 | 2.9 |

[a]ATx CBA/Ca mice were injected with equal amounts of rIgG$_{2a}$ CD4 mAb (YTS 177.9) and rIgG$_{2b}$ CD8 mAb (YTS 156.7) for 2 weeks (total mAbs 7 mg/mouse). 2 × 10$^7$ AKR bone marrow cells were infused 2 days after the beginning of mAb treatment. 8 weeks later, their spleen cells were stimulated in vitro as described in Example 2.
[b]Numbers given are counts per minute (geometric means of triplicate samples) of each individual mouse.
[c]Spleen Vβ6+ cells stained with mAb 44-22-1 (Payne et al, 1988, PNAS USA, 85, 7695) and analysed by flow cytometry.
[d]Control mice were ATx CBA injected with mAbs only.

TABLE 5

Transfer of normal lymphocytes does not break tolerance in normal mice

| ANIMALS | CELLS INJECTED[a] | GRAFT SURVIVAL AFTER CELL TRANSFER |
|---|---|---|
| Tolerant CBA | B10.BR spleen cells | >100 days × 4 |
| | naive CBA spleen cells | >100 days × 4 |
| | sensitised CBA spleen cells[c] | 15, 17, 17, 21, |
| T-depleted[b] | naive CBA spleen cell | 12, 14, 14, 15 |
| | sensitised CBA spleen cells | 8, 8, 9, 10 |
| ATx CBA | none | >100 days × 4 |

CBA/Ca mice were rendered tolerant to B10.BR skin as described in FIG. 13a legend.
[a]Mice carrying B10.BR skin for >200 days were selected and injected with 5 × 10$^7$ spleen cells intravenously.
[b]ATX CBA mice were depleted of T cells by injection of CD4 and CD8 mAbs at least 4 weeks before they were grafted with B10.BR skin.
[c]Sensitised spleen cells were from CBA mice which had been injected with B10.BR spleen cells and had rejected B10.BR skin grafts.

TABLE 6

Monoclonal antibodies used

| Monoclonal antibody | Specificity | Epitope | Isotype | Reference |
|---|---|---|---|---|
| YTS 191.1.2 | mouse CD4 | a | IgG$_{2b}$ | Cobbold et al, 1984, Nature, 312, 548 |
| YTA 3.1.2 | mouse CD4 | b | IgG$_{2b}$ | Qin et al, Eur J. Immunol. 17, 1159, 1987 |
| YTS 177.9.6 | mouse CD4 | a | IgG$_{2a}$ | |
| YTS 169.4.2 | mouse CD8 | Lyt-2 (a) | IgG$_{2b}$ | Cobbold et al, 1984, Nature, 312, 548 |
| YTS 156.7.7 | mouse CD8 | Lyt-3 (b) | IgG$_{2b}$ | Qin et al, 1989 J. Exp. Med. 169, 779 |
| YTS 105.18.10 | mouse CD8 | Lyt-2 (c) | IgG$_{2a}$ | |
| YTS 154.7.7 | mouse Thy-1 | monomorphic | IgG$_{2b}$ | Cobbold et al, 1984, Nature, 312, 548 |
| YTS 121.5.2 | mouse CD5 | Lyt-1 | IgG$_{2b}$ | Cobbold et al, 1984, Nature, 312, 548 |

TABLE 7

Remaining T-cells in CD4 + CD8 antibody treated mice

B10 tolerant CBA
Per-cent of spleen cells staining positive

| Time (days) | CD4+ | CD8+ | Thy-1+ CD5+ | anti-rat Ig* | number tested |
|---|---|---|---|---|---|
| 0 | 34 ± 2 | 16 ± 1 | 47 ± 1 | 0 ± 0 | 4 |
| 5 | 12 ± 3 | 12 ± 5 | 13 ± 4 | 6 ± 1 | 8 |
| 12 | 18 ± 4 | 18 ± 6 | 18 ± 5 | 3 ± 1 | 3 |
| 19 | 27 ± 4 | 22 ± 3 | 26 ± 5 | 3 ± 3 | 6 |
| 45 | 24 ± 5 | 11 ± 2 | 28 ± 4 | 0 ± 0 | 8 |

*Anti-rat Ig was a mixture of MAR-18.5-FITC and NORIG-7.16-FITC.

All mice received rat IgG$_{2b}$ CD4 and CD8 followed by rat IgG$_{2a}$ CD4 and CD8 as described in Example 2 from day 0–21.

TABLE 8

Serum levels of active IgG$_{2a}$ CD4 and CD8 monoclonal antibodies

| Time | CD4 serum antibody (ng/ml) [Four individual mice] | | | | CD8 serum antibody (ng/ml) [Four individual mice] | | | |
|---|---|---|---|---|---|---|---|---|
| Day 0 | <0.5 | <0.5 | <0.5 | <0.5 | <10 | <10 | <10 | <10 |
| Day 12 | >100 | >100 | >100 | >100 | >100 | 120 | 150 | >1000 |
| Day 19 | 50 | >100 | >100 | >100 | 190 | >1000 | >1000 | >1000 |
| Day 29 | 50 | >100 | >100 | >100 | 75 | 250 | >1000 | >1000 |
| Day 32 | 80 | 90 | >100 | >100 | 500 | 600 | >1000 | >1000 |

TABLE 8-continued

Serum levels of active IgG$_{2a}$ CD4 and CD8 monoclonal antibodies

| | CD4 serum antibody (ng/ml) [Four individual mice] | | | | CD8 serum antibody (ng/ml) [Four individual mice] | | | |
|---|---|---|---|---|---|---|---|---|
| Day 36 | 5 | 100 | >100 | >100 | 60 | 85 | 500 | >1000 |
| Day 43 | <0.5 | 15 | 70 | >100 | <10 | <10 | 12 | 25 |
| Day 46 | <0.5 | <0.5 | <0.5 | 1.0 | <10 | <10 | <10 | <10 |
| Day 60 | <0.5 | <0.5 | <0.5 | <0.5 | <10 | <10 | <10 | <10 |
| Day 78 | <0.5 | <0.5 | <0.5 | <0.5 | <10 | <10 | <10 | <10 |

Monoclonal antibody treatment was rat IgG$_{2b}$ CD4 and CD8 on days 0 and 2, followed by rat IgG$_{2a}$ CD4 and CD8 three times per week until day 21 (2 mg total per injection).

TABLE 9

Proliferation of Peripheral Blood Lymphocytes from B10 tolerant CBA mice
Proliferation ($^{125}$IUDR incorporation) to stimulators

| Group | CBA (cpm.) | BALB/c (cpm.) | B10 (cpm.) |
|---|---|---|---|
| Normal CBA control | 370 + 236 −121 | 4952 + 5236 −2624 | 2210 + 2622 −1285 |
| B10 tolerant CBA | 716 + 800 −448 | 4952 + 3470 −2091 | 3592 + 2875 −1656 |

Individual B10 tolerant CBA/Ca mice, or normal controls, were bled from the tail vein on day 78.

Proliferation of peripheral blood cells was determined as in Example 2.

Figures given are logarithmic means and standard deviations of six mice per group.

We claim:

1. A method of treating in a human a disorder mediated by an immune reaction to an antigen possessed by said human and presented to CD4+ T-cells within said human, said method comprising administering to said human an amount of a non-depleting anti-CD4 monoclonal antibody and a non-depleting anti-CD8 monoclonal antibody sufficient to induce long term specific immunological unresponsiveness to said antigen thereby effecting said treatment.

2. The method of claim 1 further comprising administering to said human a therapeutically effective amount of one or more immunosuppressive agents.

3. The method of claim 2 wherein said immunosuppressive agent is an immunosuppressive antibody, a steroid, cyclosporin or anti-lymphocyte globulin.

4. A method of treating, in a human, a disorder mediated by an immune reaction to a self antigen, said method comprising administering to a human in need of said treatment an amount of a non-depleting anti-CD4 monoclonal antibody sufficient to induce long term specific immunological unresponsiveness to said antigen thereby effecting said self treatment.

5. The method of claim 4 further comprising administering to said human a therapeutically effective amount of one or more immunosuppressive agents.

6. The method according to claim 4 wherein said human suffers from rheumatoid arthritis or multiple sclerosis.

7. The method according to claim 6 wherein said human suffers from rheumatoid arthritis.

8. The method according to claim 4 wherein said method comprises administering an amount of an antibody-binding site containing fragment of a non-depleting anti-CD4 monoclonal antibody sufficient to effect said treatment.

9. The method of claim 5 wherein said immunosuppressive agent is an immunosuppressive antibody, a steroid, cyclosporin or anti-lymphocyte globulin.

* * * * *